United States Patent
Anelli et al.

(10) Patent No.: US 6,461,588 B1
(45) Date of Patent: *Oct. 8, 2002

(54) USE OF BILE ACID CONJUGATES, DERIVATIVES THEREOF WITH METAL COMPLEXES AS BLOOD POOL AGENTS FOR NUCLEAR MAGNETIC RESONANCE DIAGNOSTICS

(75) Inventors: Pier Lucio Anelli; Marino Brocchetta; Christoph De Haen; Ornella Gazzotti; Luciano Lattuada; Giovanna Lux; Giuseppe Manfredi; Pierfrancesco Morosini; Daniela Palano; Michele Serleti; Fulvio Uggeri; Massimo Visigalli, all of Milan (IT)

(73) Assignee: Bracco Imaging S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/318,618

(22) Filed: May 26, 1999

(30) Foreign Application Priority Data

Dec. 23, 1998 (IT) .......................................... MI98A2802

(51) Int. Cl.[7] ................................................ A61B 5/055
(52) U.S. Cl. ........................ 424/9.365; 534/15; 424/9.1; 424/9.36; 424/1.65; 424/9.3
(58) Field of Search ................................. 424/9.1, 1.11, 424/1.65, 9.3, 9.36, 9.365, 9.35; 534/7, 10–16; 552/500, 502, 541, 548, 549, 551, 552

(56) References Cited

U.S. PATENT DOCUMENTS 6,010,681 A * 1/2000 Margerum et al. ......... 424/9.35

FOREIGN PATENT DOCUMENTS

WO 9532741 * 12/1995

* cited by examiner

*Primary Examiner*—Dameron L. Jones
(74) *Attorney, Agent, or Firm*—Nixon & Vanderhye P.C.

(57) ABSTRACT

Blood pool imaging contrast agents containing paramagnetic bi- and tri-valent metal ion chelates of bile acid conjugates with molecules having chelating activity are used in magnetic resonance imaging of the vascular system and particularly the coronaries.

6 Claims, 2 Drawing Sheets

Scheme 2

Scheme 3

USE OF BILE ACID CONJUGATES, DERIVATIVES THEREOF WITH METAL COMPLEXES AS BLOOD POOL AGENTS FOR NUCLEAR MAGNETIC RESONANCE DIAGNOSTICS

BACKGROUND OF THE INVENTION

The present invention relates to the novel use of metal ion chelates of bile acid conjugates with molecules having chelating activity as contrast agents in the diagnostic technique known as "magnetic resonance imaging" (M.R.I.), in particular as blood pool agents.

Complexes formed of chelating agents and suitable metals are already used as contrast agents in the following diagnostic techniques: X-ray imaging, nuclear magnetic resonance imaging (M.R.I.) and scintigraphy.

In particular, medical diagnosis using magnetic resonance imaging (M.R.I.), a recognizedly powerful diagnostic technique in clinical practice (Stark, D. D., Bradley, W. G., Jr., Eds. "Magnetic Resonance Imaging" The C. V. Mosby Company, St. Louis, Mo. (USA), 1988), mainly employs paramagnetic pharmaceutical compositions, preferably containing chelated complexes of bi-trivalent paramagnetic metal ions with polyaminopolycarboxylic ligands and/or their derivatives or analogues.

The images basically coming from the NMR signal of water protons are the result of a complex interaction between different parameters, such as proton density and $T_1$ and $T_2$ relaxation times. A contrast enhancement can be obtained through the administration of exogenous chemical substances which significantly change the resonance properties of nearby water protons (see Lauffer, R. B. Chem. Rev. 1987, 87, 901).

The paramagnetic contrast agents used for N.M.R imaging act modifying the relaxation times of the water protons present in the tissues in which said contrast agent is concentrated, and they can therefore increase the contrast between different tissues, or between healthy and diseased tissues.

Gadolinium paramagnetic complexes, due to their high capability of reducing relaxation times of the protons of nearby water molecules through dipolar interaction, have been the object of studies, publications and patents.

Some of them are at present in clinical use as M.R.I. contrast agents:

Gd-DTPA, N-methylglucamine salt of the gadolinium complex with diethylenetriaminopentaacetic acid, MAGNE-VIST®; Gd-DOTA, N-methylglucamine salt of the gadolinium complex with 1,4,7,10-tetraazacyclododecane-1,4,7, 10-tetraacetic acid, DOTAREM®; Gd-HPDO3A, gadolinium complex with [10-(2-hydroxypropyl)-1,4,7,10-tetraazacyclododecane-1,4,7-triacetic acid, PROHANCE®; Gd-DTPA-BMA, gadolinium complex with diethylenetriaminopentaacetic acid bis(methylamide), OMNISCAN®.

The contrast agents listed above and commercially available are intended for a general use. In fact, after administration, the said M.R.I. contrast agents diffuse in blood and in the extracellular areas of various parts of the body before being excreted. They are therefore similar, in this respect, to the iodinated compounds used for X-ray medical diagnosis.

At present the medical profession is in need of contrast agents that are aimed at specific organs or for imaging of the blood system, which cannot be well defined by means of the usual products already commercially available. The first approach to obtain the latter consisted in covalently linking the contrast agent to macromolecules, such as proteins, or in inglobating it inside stable molecular aggregates such as liposomes, or still in using the so-called superparamagnetic particles.

For example, the gadolinium complex with diethylenetriaminopentaacetic acid (Gd-DTPA) was linked to human albumin (HSA), polylysine or dextran (Oksendal A. N. et al., J. Magn. Reson. Imaging, 157, 1993; Rocklage S. M., "Contrast Agents, Magn. Res. Imaging, Mosby Year Book, 372–437, 1992) in order to minimize or even suppress the diffusion from blood into the extracellular fluid thus providing a higher retention of the agent in the blood system. Such an approach, although attaining the desired effect, suffers from disagreeable side effects as the agent itself is excreted with difficulty.

A different strategy is the use of superparamagnetic particles coated with polyethylene glycols or hydrocarbons in order to reduce the hepatic uptake by endothelial reticulum or by other systems (Tilcock C., Biochim. Biophys. Acta, 77, 1993; Bogdanoy A. A. et al., Radiology, 701, 1993), thus prolonging the permanence of said agents in blood. In this case also the above mentioned side effects occur, as well as problems due to the high production cost.

The demand for an efficient blood pool agent, having low toxicity and reasonably economic costs, is therefore still unmet.

The present invention relates to the novel use as blood pool agents of specifically selected compounds, already previously described by the Applicant in international patent application WO-A-95/32741, resulting from the conjugation of a bile acid with a chelating agent, which are capable of chelating the ions of paramagnetic bi-trivalent metals, as well as novel compounds, the process for the preparation thereof and the use thereof as blood pool agents.

Said compounds have shown a good hepatobiliary excretion (see Rings P. L. et al., Acta Radiologica, 38, 125, 1997) which makes them promising contrast agents for visualizing the hepatobiliary system.

It has now surprisingly been found that a specific class of said compounds remains in the vascular system for a sufficiently long time so as to be valuable for use as contrast agents for the imaging of the vascular system, particularly of coronaries.

This effect can be clearly evidenced carrying out in vivo tests in animals (such as rabbit, monkey). The permanence in the vascular system can in fact be immediately visualized when plotting the proton relaxation values ($1/T_1$) of blood samples of the animal, taken at appropriate time intervals after administration of the contrast agent.

As Gd(III) complexes are among the preferred paramagnetic species, high $1/T_1$ values are evidence of high concentrations of the contrast agent in blood.

The difference between a conventional extracellular contrast agent and a blood pool agent, is well clarified in the paper by Lauffer et al., Radiology, 529,1998 in which $T_1$ profiles in blood as a function of time elapsed after the administration of the contrast agent are reported.

In particular, the complexes of the present invention, when administered for example to the rabbit at a dosage compatible with a reasonable safety index, are capable of inducing changes in relaxation rates (measured in $\Delta 1/T_1$) in blood higher than 5 s$^{-1}$ 10 minutes after administration, thus being promising for use as contrast agents for the imaging of the vascular system.

It has been found that this type of effect cannot be solely related to the presence of bile acids, but it depends on the chemical structure of said complexes. It seems, in fact, that the chelating unit should be preferably linked to the steroidal skeleton through a bond at the 3,7 or 12 positions of the bile acid.

It has, in fact, been proved that any linkage between the chelating unit and the bile acid involving the carboxylic group at the 24 position would yield complexes having unsatisfactory permanence in the vascular system.

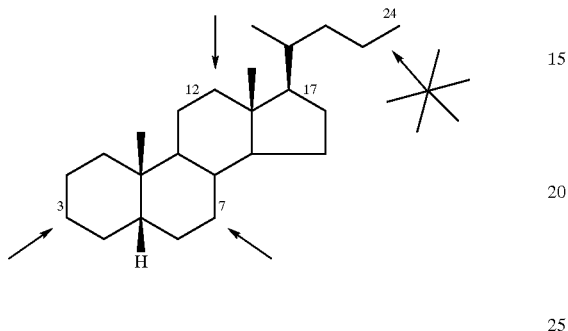

BRIEF DESCRIPTION OF THE DRAWINGS

The invention is further illustrated in the attached figures in which.

DESCRIPTION OF THE INVENTION

Figure 1:
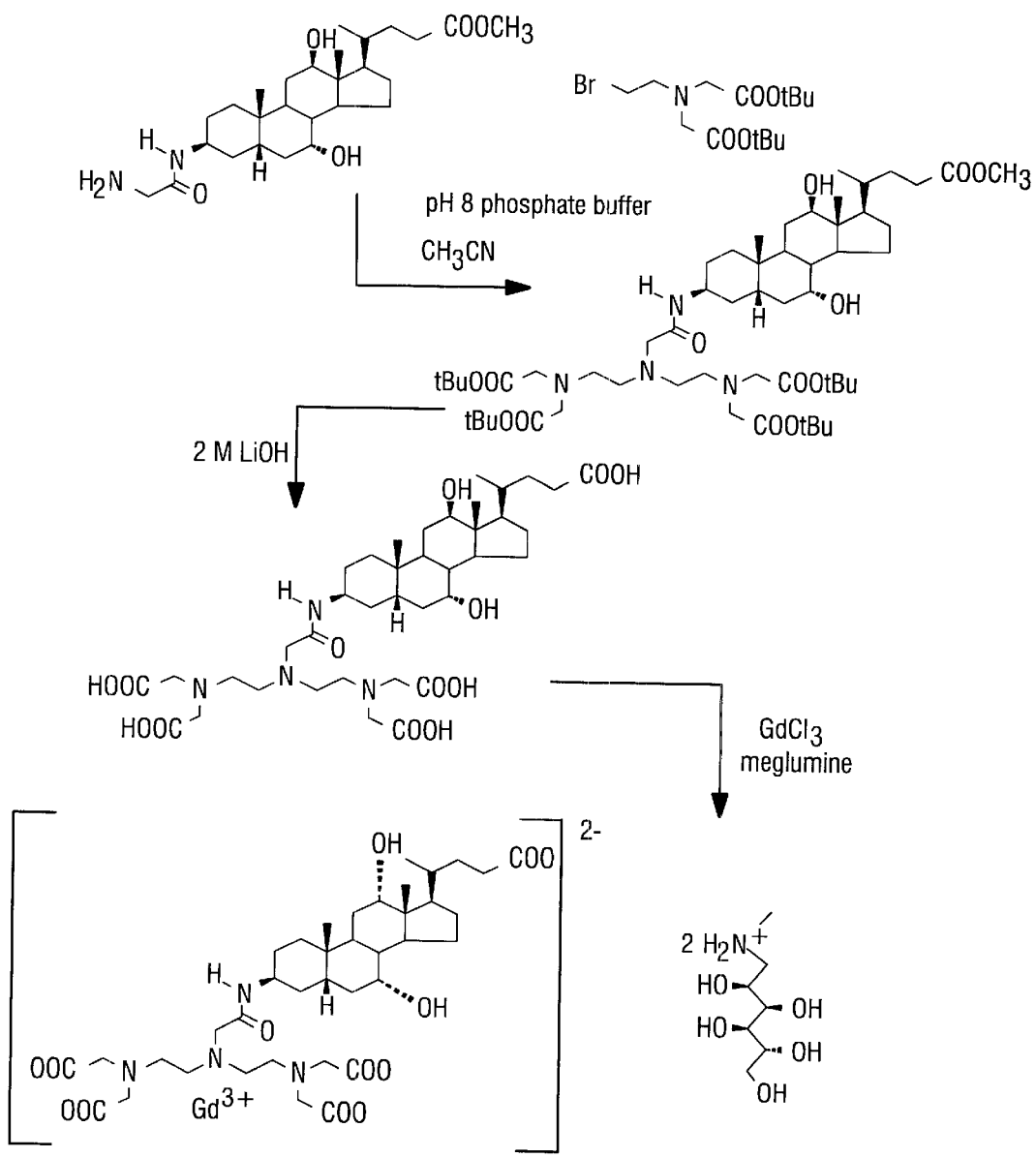
FIG. 1 is a reaction scheme illustrating the synthesis of the compound of Example 2.

It is therefore an object of the present invention the use as blood pool agents of the complexes of the compounds of general formula (I) with paramagnetic bi-trivalent metal ions selected the group consisting of $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $Yb^{(3+)}$ or $Mn^{(2+)}$, $$X-L-Y \quad (I),$$

in which

X is the residue of a polyaminopolycarboxylic ligand or derivatives thereof, selected from the group consisting of: ethylenediaminotetraacetic acid (EDTA), diethylenetriaminopentaacetic acid (DTPA), 1,4,7,10-tetraazacyclododecane-1,4,7,10-tetraacetic acid (DOTA), 1,4,7,10-tetraazacyclododecane-1,4,7-triacetic acid (DO3A), [10-(2-hydroxypropyl)-1,4,7,10-tetraazacyclododecane-1,4,7-triacetic acid (HPDO3A), 4-carboxy-5,8,11-tris(carboxymethyl)-1-phenyl-2-oxa-5,8,11-triazatridecan-13-oic acid (BOPTA);

Y is the derivative of a bile acid selected from the group consisting of residues of cholic, chenodeoxycholic, deoxycholic, ursodeoxycholic, lithocholic acids,

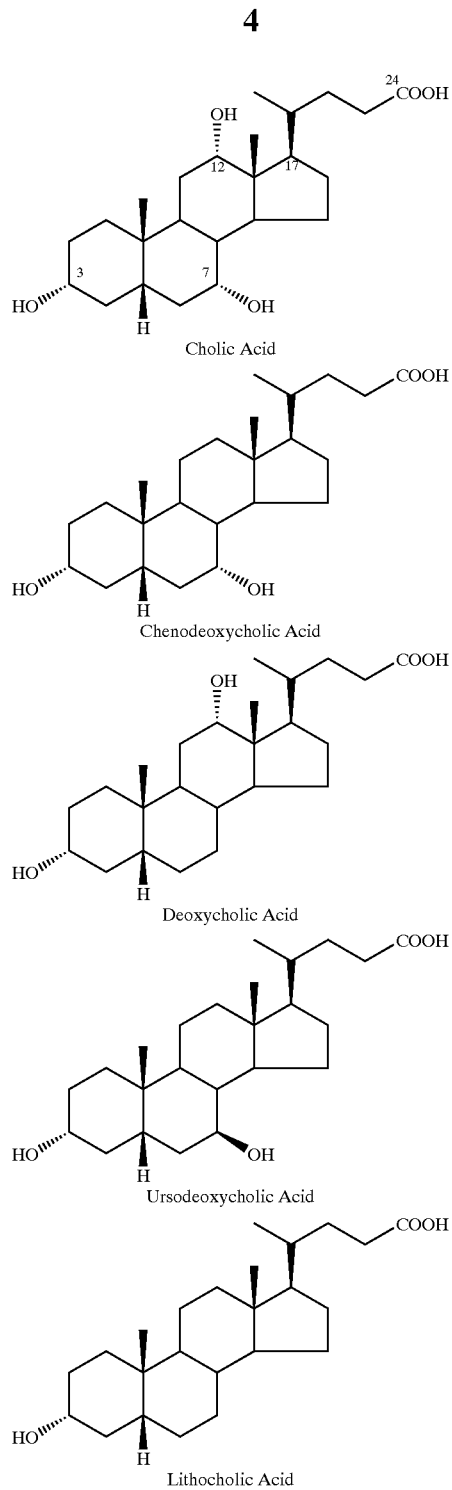

Cholic Acid

Chenodeoxycholic Acid

Deoxycholic Acid

Ursodeoxycholic Acid

Lithocholic Acid both as they are and functionalized at the positions having the hydroxy group as the reactive group, independently of the stereochemistry of the final products, said derivative also comprising the conjugate of the acid group at the 24 position with taurine and glycine;

L is a chain linked at any position of X, optionally comprising one of the carboxylic groups which is thus transformed into an amido group, and the C-3, C-7, C-12 positions of Y, and it has the following formula (II)

 (II)

in which
m is an integer ranging from 1 to 10, wherein for values above 1, A can have different meanings,
A has the following formula (III),

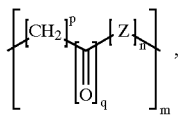 (III)

n and q can be 0 or 1, but they are not at the same time zero,
p can range from 0 to 10,
Z is an oxygen atom or a —NR group, in which
R is a hydrogen atom, or a ($C_1$–$C_5$) alkyl group unsubstituted or substituted by a group —COOH.

Particularly preferred compounds are those in which the spacing chains L have the following general formulae (IIIa) and (IIIb).

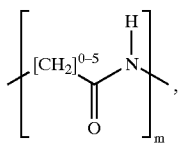 (IIIa)

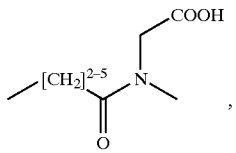 (IIIb)

Also preferred are the structures in which Z is the oxygen atom and therefore L is formed through the hydroxy groups present at the 3, 7, 12 positions, independently of the stereochemistry of the final products.

Particularly preferred are the compounds of formula (I) in which the residue X is selected from the group consisting of: EDTA, DTPA, DOTA, DO3A, BOPTA; L is selected from the group consisting of (IIIa), (IIIb);

Y is preferably selected from the group consisting of residues of cholic, deoxycholic, chenodeoxycholic, litho-cholic acids, linked to L by an amino group at the 3-position and the acid group at the 24 position is present as it is or as its taurine or glycine derivative.

Y can also be differently functionalized, for example through conversion of one or more hydroxy groups to keto groups.

Particularly preferred complexes with paramagnetic metal ions defined above are the complexes with gadolinium or with manganese.

Preferred are the compounds of general formula (IV), in which in general formula (I) the residue X is DTPA substituted on the central chain and in which $R_1$ is a hydrogen atom or the group —COOH,

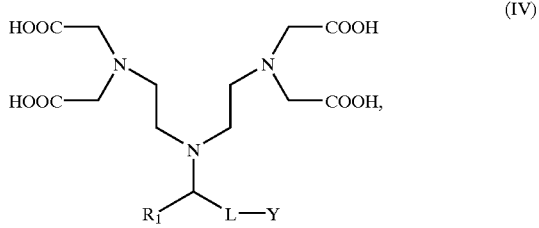 (IV)

Y is selected from the group consisting of cholic, deoxycholic, chenodeoxycholic, lithocholic residues and L has the structure of formula (III).

Particularly preferred are compounds of general formula (IVa)

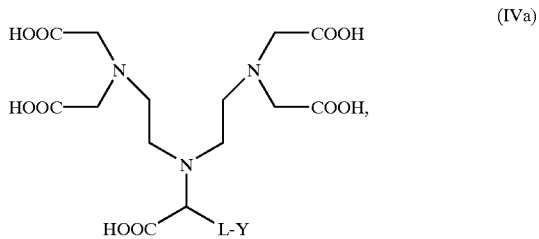 (IVa)

in which $R_1$ is the group —COOH and Y has the meanings defined above for the compounds of general formula (IV) and L has the structures (IIIa) and (IIIb).

Further objects of the present invention are the following novel compounds, as well as the processes for the preparation thereof, belonging to the class of general formula (IVa);
[[3β(S),5β]-3-[[4-[bis[2-[bis(carboxymethyl)amino]ethyl]amino]-4-carboxy-1-oxo-butyl](carboxymethyl)amino]cholan-24-oic acid

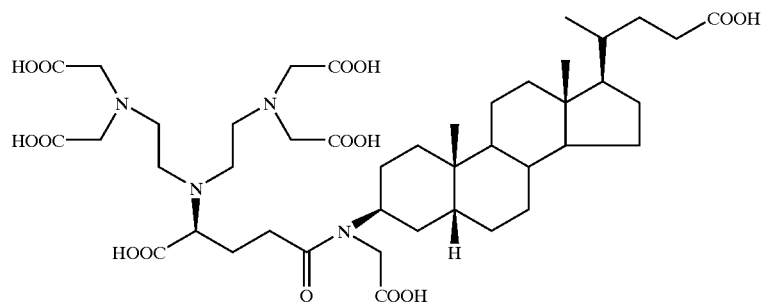

[3β(S),5β]-3-[[4-[bis[2-[bis(carboxymethyl)amino]ethyl]amino]-4-carboxy-1-oxobutyl]amino]cholan-24-oic] acid;
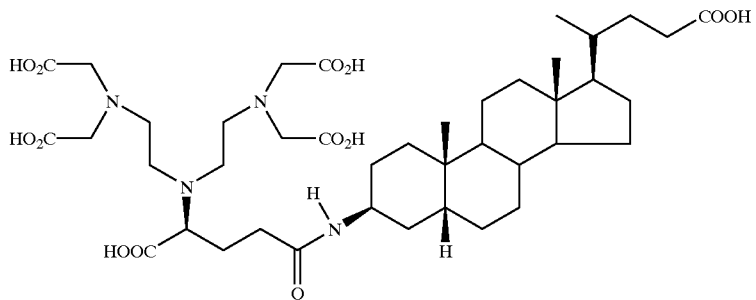
[3β(S),5β]-3-[[4-[bis[2-[bis(carboxymethyl)amino]ethyl]amino]-4-carboxy-1-oxobutyl]amino]-12-oxocholan-24-oic acid;
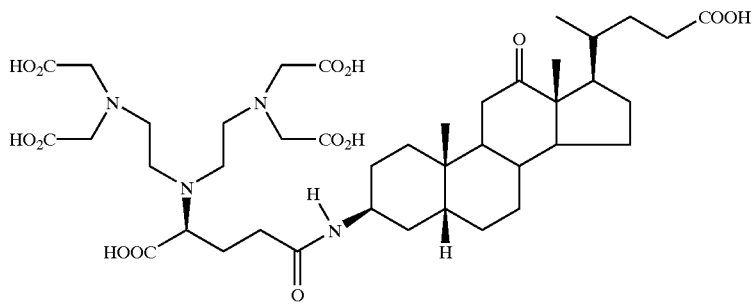
[3β(S)-5β,7α]-3-[[4-[bis[2-[bis(carboxymethyl)amino]ethyl]amino]-4-carboxy-1-oxobutyl]amino]-7-hydroxycholan-24-oic acid;
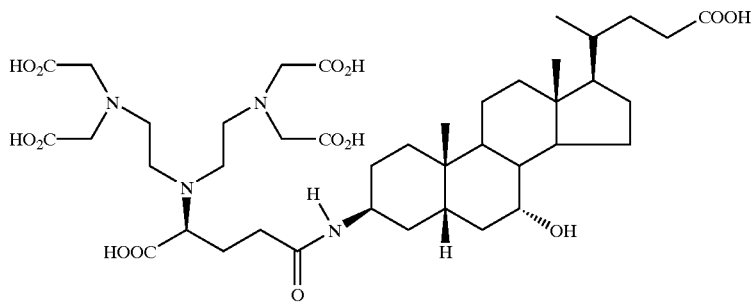

2-[[[3β(S),5β]-3-[[4-[bis[2-[bis(carboxymethyl)amino]
ethyl]amino]-4-carboxy-1-oxobutyl]amino]-24-
oxocholan-24-yl]amino]ethanesulfonic acid;

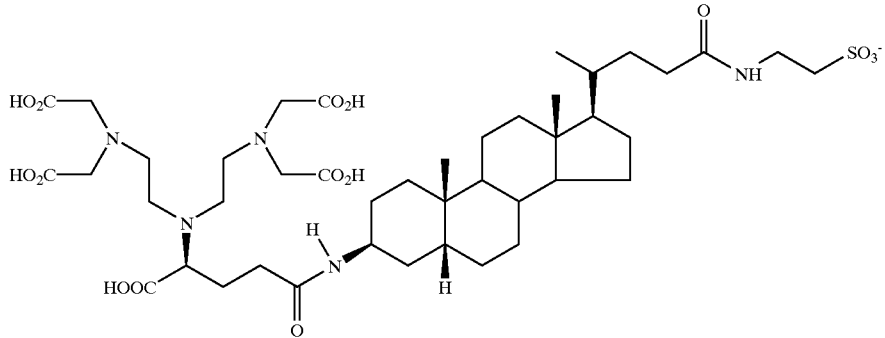

[3β(S),5β,12α]-3-[[4-[bis[2-[bis(carboxymethyl)amino]
ethyl]amino]-4-carboxy-1-oxobutyl]amino]-12-
hydroxycholan-24-oic acid;

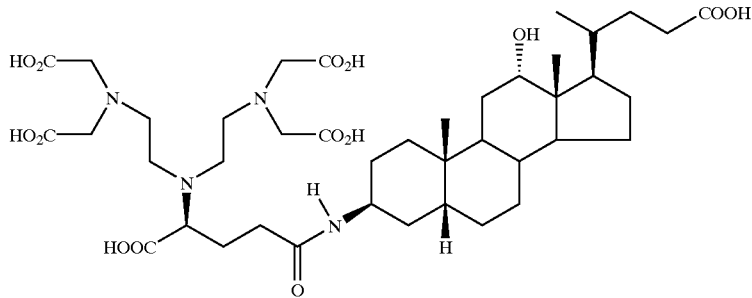

[3α(S),5β]-3-[2-[[5-[bis[2-[bis(carboxymethyl)amino]
ethyl]amino]-5-carboxypentyl]amino]-2-oxoethoxy]
cholan-24-oic acid.

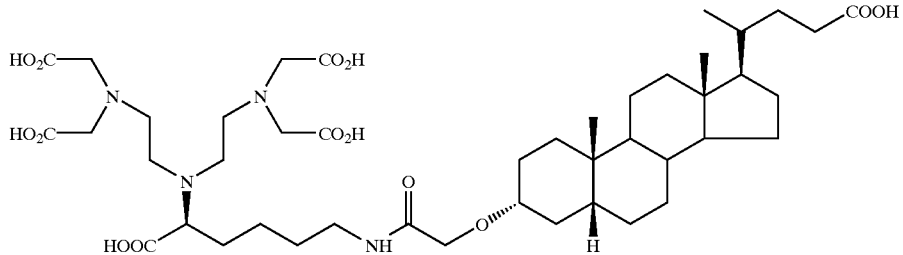

Other compounds belonging to this class, whose complexes with gadolinium have been described in patent application WO-A-95/32741, are the following:

[3β(S),5β,7α,12α]-3-[[4-[bis[2-[bis(carboxymethyl)amino]
ethyl]amino]-4-carboxy-1-oxobutyl]amino]-7,12-
dihydroxycholan-24-oic acid;

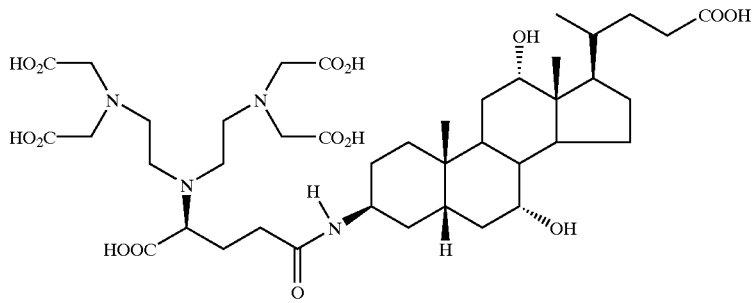

[3β(S),5β,7α,12α]-3-[[4-[[5-[bis[2-[bis(carboxymethyl)amino]ethyl]amino]-5-carboxypentyl]amino]-1,4-dioxobutyl]amino]-7,12-dihydroxycholan-24-oic acid.

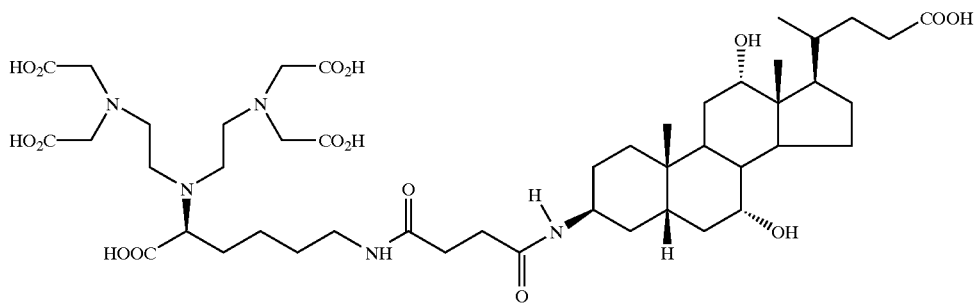

Also preferred are the compounds of general formula (IVb), which also are DTPA derivatives substituted at the central position,

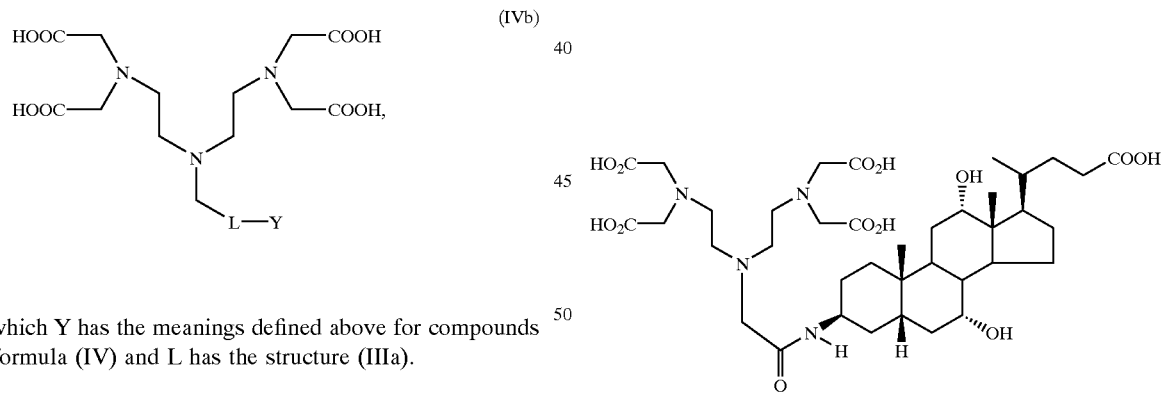

in which Y has the meanings defined above for compounds of formula (IV) and L has the structure (IIIa).

The present invention further relates to the following novel compounds, as well as to the process for the preparation thereof, which compounds belong to the class of general formula (IVb):

(3β,5β,7α,12α)-3-[[[bis[2-[bis(carboxymethyl)amino]ethyl]amino]acetyl]amino]-7,12-dihydroxycholan-24-oic acid (3β,5β)-3-[[[[[bis[2-[bis(carboxymethyl)amino]ethyl]aminolacetyl]amino]acetyl]amino]cholan-24-oic acid

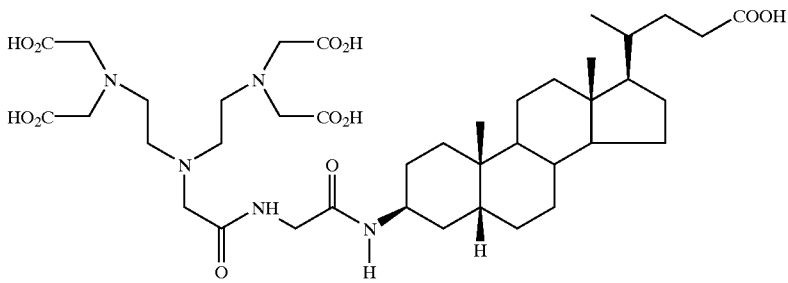

Other compounds belonging to this class, whose complexes with gadolinium have been described in patent application WO-A-95/32741, are the following:
(3β,5β,7α,12α)-3-[[[[[bis[2-[bis(carboxymethyl)amino]ethyl]amino]acetyl]amino]acetyl]amino]-7,12-dihydroxycholan-24-oic acid;

Other compounds belonging to this class, whose complexes with gadolinium have been described in patent application WO-A-95/32741, are the following:
(3β,5β,7α,12α)-3-[[N-[N-[2-[[2-[bis(carboxymethyl)amino]ethyl](carboxymethyl)amino]ethyl]-N-(carboxymethyl)glycyl]glycyl]amino]-7,12-dihydroxycholan-24-oic acid;

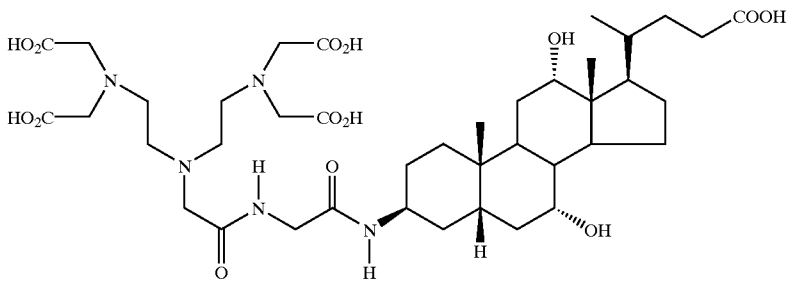

(3β,5β,7α,12α)-3-[[6-[[[bis[2-[bis(carboxymethyl)amino]ethyl]amino]-acetyl]amino]-1-oxohexyl]amino]-7,12-dihydroxycholan-24-oic acid.

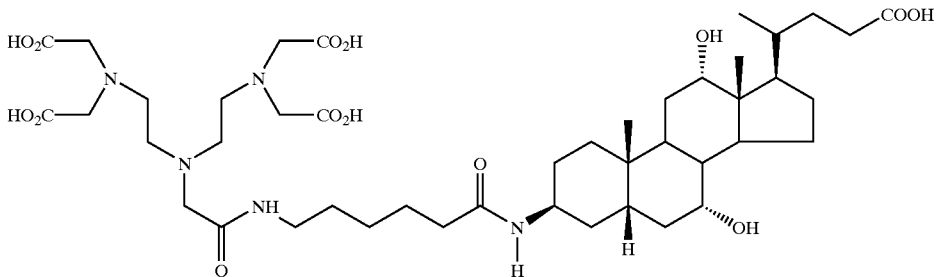

Particularly preferred also are the compounds of general formula (V), in which in general formula (I) the residue X is DTPA, Y has the meanings defined above for compounds (IV) and L has the structure of formula (IIIa).

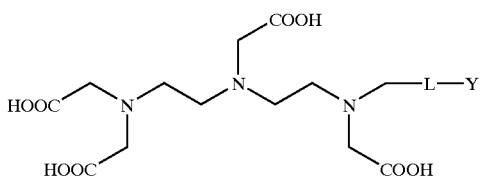

(V)

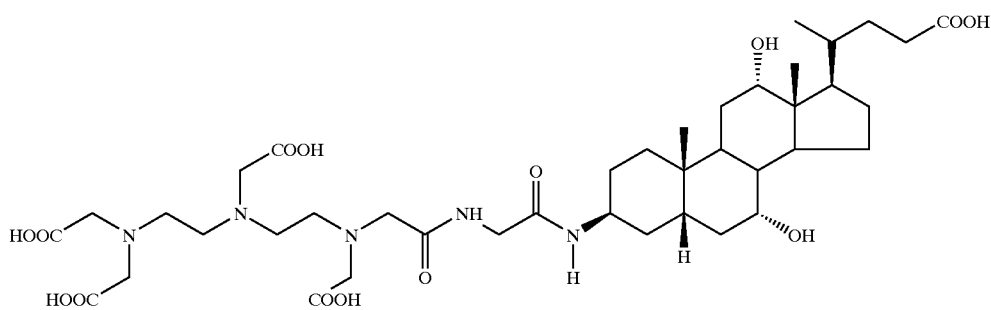

18-[[(3β,5β,7α,12α)-23-carboxy-7,12-hydroxy-24-norcholan-3-yl]amino]-3,6,9-tris(carboxymethyl)-11,18-dioxo-3,6,9,12-tetraazaoctadecanoic acid.

Similarly, the compounds of general formula (VII) are preferred, in which in formula (I) the residue X is EDTA, Y

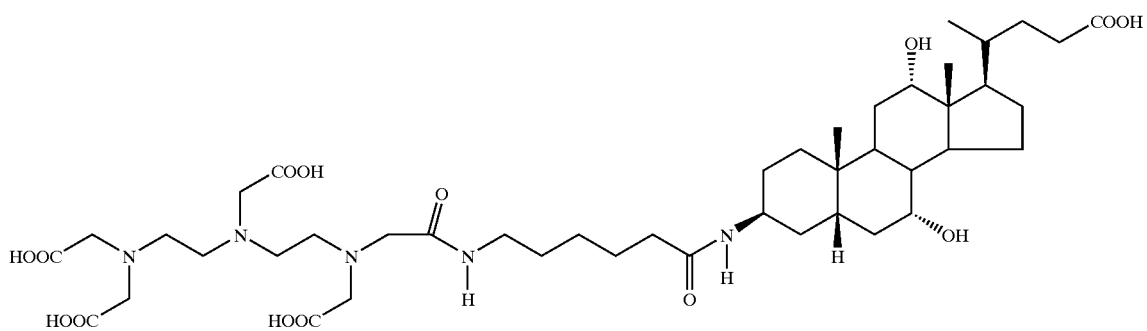

Also preferred are the compounds of formula (VI), in which in formula (I) the residue X is DO3A, Y has the meanings defined above for compounds of formula (IV) and L is selected from the structures (IIIa) and (IIIb).

has the meanings defined above for compounds of formula (IV) and L has the structure of formula (IIIa).

Particularly preferred are the complexes of compounds of formula (VII) with manganese.

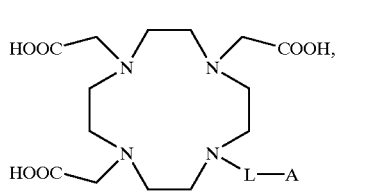

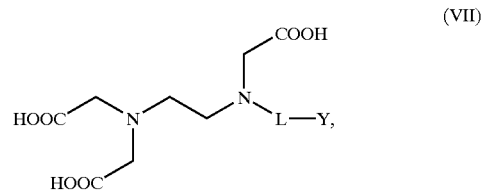

Among the compounds of formula (VI), particularly preferred is 10-[3-[[(3α,5β,7α,12β)-23-carboxy-7,12-dihydroxy-24-norcholan-3-yl]oxy]-2-hydroxypropyl]-1,4,7,10-tetraazacyclododecane-1,4,7-triacetic acid, whose complex with gadolinium has been described in patent application WO-A-95/32741.

Among the compounds of formula (VII) particularly preferred are the following:
[3β(S),5β,7α,12α]-3-[[4-[[5-[[2-[bis(carboxymethyl)amino]ethyl](carboxymethyl)amino]-5-carboxypentyl]amino]-1,4-dioxobutyl]amino]-7,12-dihydroxycholan-24-oic acid

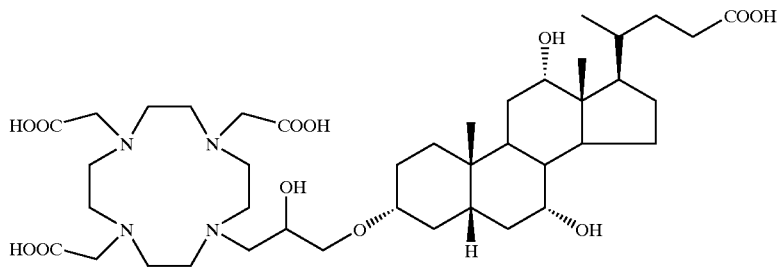

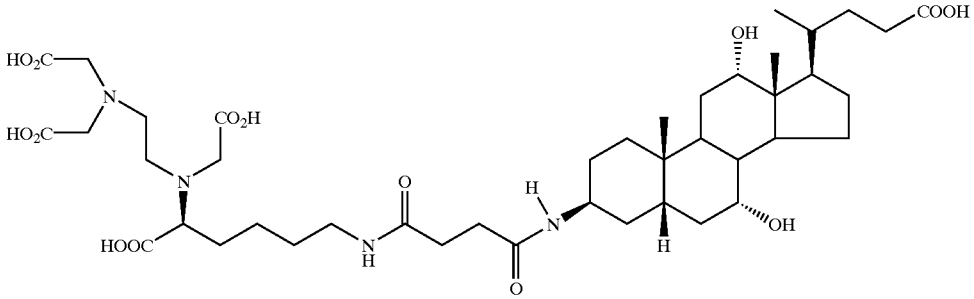

[3β(S),5β]-3-[2-[[5-[[2-[bis(carboxymethyl)amino]ethyl]
(carboxymethyl)amino]-5-carboxypentyl]amino]-2-
oxoethoxy]-cholan-24-oic acid

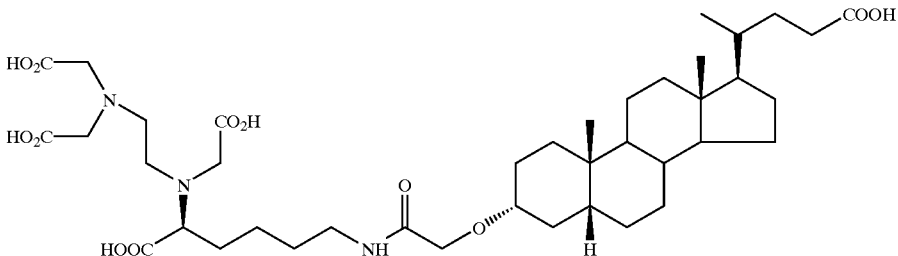

[3β(S),5β,12α]-3-[[4-[[2-[[bis(carboxymethyl)amino]ethyl]
(carboxymethyl)amino]-4-carboxy-1-oxobutyl]amino]-
12-hydroxycholan-24-oic acid

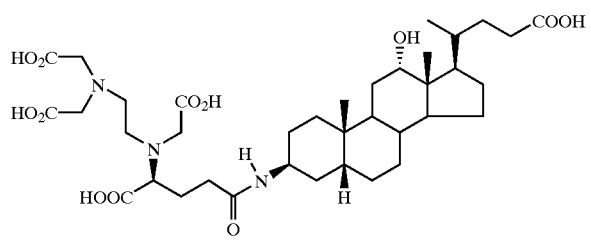

[3β(S),5β]-3-[[4-[[2-[[bis(carboxymethyl)amino]ethyl]
(carboxymethyl)amino]-4-carboxy-1-oxobutyl]amino]-
12-oxocholan-24-oic acid

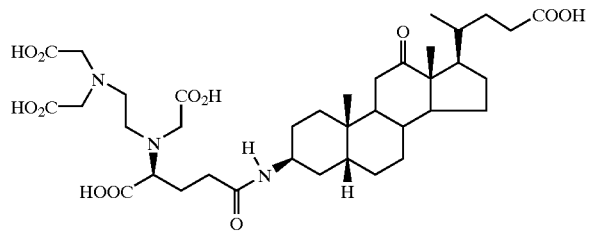

The compounds of general formula (I) can be prepared with the method of convergent synthesis which comprises:

1) synthesis of a functionalized ligand, i.e. of a ligand capable of coordinating one paramagnetic metal ion while binding stably to the bile acid by means of a suitable functional group;
2) synthesis of a functionalized bile acid;
3) coupling reaction between two different syntons;
4) cleavage of any protective groups;
5) complexation of the paramagnetic metal ion; illustrated in detail in the above cited patent application WO-A-95/32741.

Some of the preferred processes for the preparation of the ligands of the present invention involve the formation of an amido bond between two syntons, one of them being the precursor of the chelating system of the paramagnetic ion (Synton A), the other being the precursor of the bile acid residue contained in the final complex (Synton B).

The methods described hereinbelow should not be considered limiting the synthesis of the compounds of the present invention.

The amido bond can be formed:

a) by reacting Syntons A containing a carboxylic function with Syntons B containing a primary or secondary amino function;
b) by reacting Syntons A containing a primary or secondary amino function with Syntons B containing a carboxylic function;
c) by reacting DTPA dianhydride (commercially available product) with a Synton B containing a primary or secondary amino function.

A list of some of syntons A and B used for this invention is reported in the following Table.

TABLE

| Synton A | Synton B |
|---|---|

The Syntons used are of course suitably protected at those groups which could give rise to parasitic reactions under the conditions used for the formation of the amido bond. After formation of the bond between the two syntons, one or more deprotection steps for restoring the original groups should be contemplated.

Figure 2:
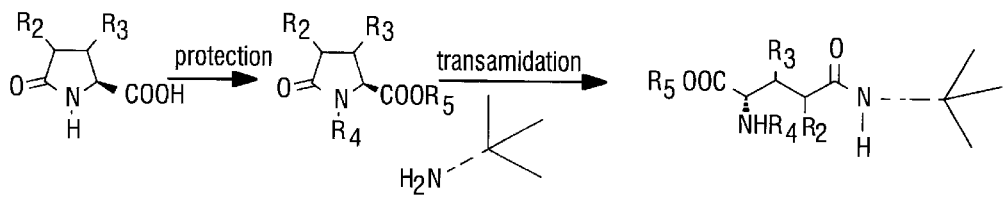
FIG. 2 is a reaction scheme illustrating the synthesis of the compounds of the invention using a transamidation reaction.

Alternatively to this type of processes, the chelating subunit can be introduced by multi-step reactions starting from a bile acid derivative, as in the case of the synthesis of the compound described in Example 2 of the Experimental section, illustrated in the following Scheme 1 in FIG. 1. The present invention also relates to a novel process illustrated in the following Scheme 2 in FIG. 2:
in which $R_4$ is a amino-protecting group;

$R_5$ is a straight or branched $C_1$–$C_{10}$ alkyl or aryl, $R_2$ and $R_3$ are independently a hydrogen atom, straight or branched $C_1$–$C_{20}$ alkyl, unsubstituted or substituted by aryl groups, or said groups form a $C_3$–$C_{10}$ cycle;

which process makes use of a transamidation reaction and allows to keep the stereochemistry at the chiral centre adjacent to the nitrogen atom of the starting pyrrolidinone and the formation of a secondary amide. The combined selection of groups $R_4$ and $R_5$ is important in that the cleavage should take place under diversified conditions. Possible examples of $R_4$ are the carbobenzyloxy (Cbz) group and of $R_5$ are the methyl group or the t-butyl group.

This process is applicable generally in order to obtain glutamic acid γ-amides and it is very useful and advantageous for the preparation of the compounds of the invention, in particular glutamic acid γ-amides with 3-amino derivatives of residues Y, as defined above. In fact, it allows to obtain the final compound avoiding the use of the expensive condensing agents for the formation o f the γ-amido bond between glutamic acid and the corresponding amine.

Figure 3:
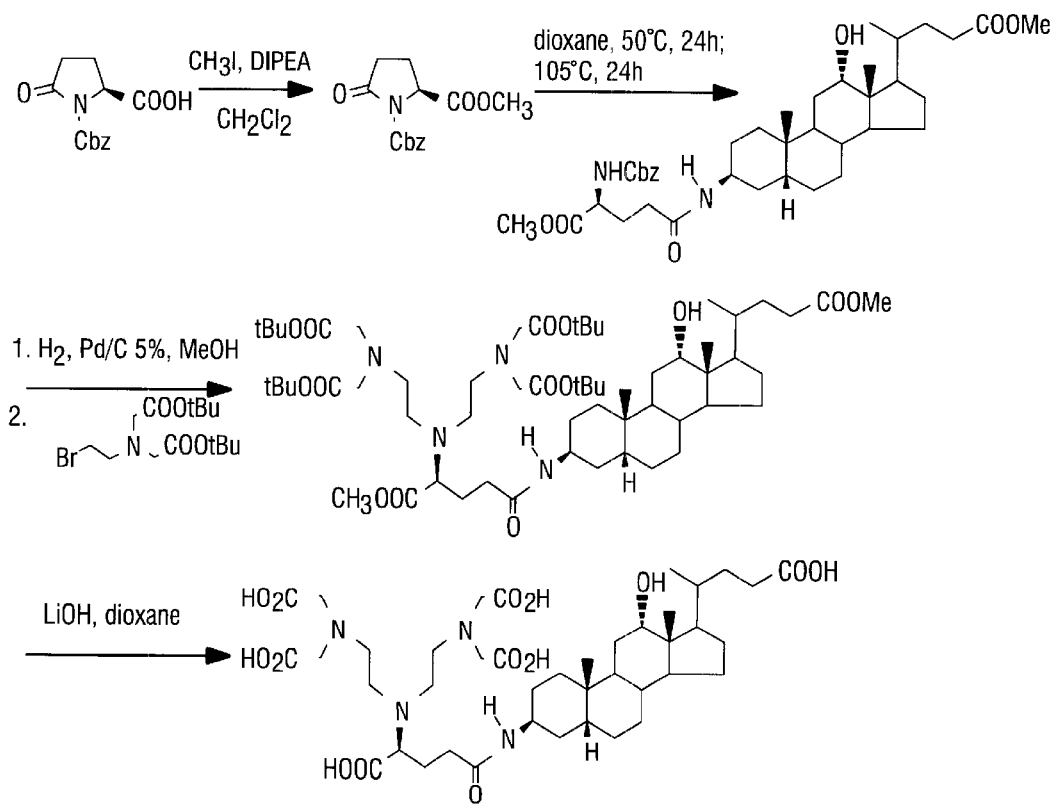
FIG. 3 is a reaction scheme illustrating the synthesis employed in Example 5.

An example of the application of this entirely novel synthetic procedure is the synthesis of [3β(S),5β,7α,12α]-3-[[4-[bis[2-[bis(carboxymethyl)amino]ethyl]amino]-4-carboxy-1-oxobutyl]amino]-12-hydroxycholan-24-oic acid, whose conventional synthesis is reported in Example 4 of the Experimental section, whereas the alternative one is reported in Example 5 and the complete synthetic scheme is shown in the following Scheme 3 in FIG. 3.

Analogously was prepared the cholic acid derivative already described in patent application WO-A-95/32741, [3β(S),5β,7α,12α]-3-[[4-[bis[2-[bis(carboxymethyl)amino]ethyl]amino]-4-carboxy-1-oxobutyl]amino]-7,12-dihydroxycholan-24-oic acid.

Metal ions suitable to form complex salts with the chelating agents of general formula (I) are the bivalent or trivalent ions of the elements selected from the group consisting of: $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $Yb^{(3+)}$ or $Mn^{(2+)}$.

As for the diagnostic use of the novel chelated complexes of the invention, they can be used as contrast agents, particularly for use as blood pool agents in the imaging diagnostic technique by means of magnetic resonance.

The preparation of the complexes is carried out conventionally, according to a process in which the oxide or the suitable salt of the paramagnetic metal, dissolved in water or suspended in a water-alcohol solution, is added to an aqueous or water-alcohol solution of the chelating agent, stirring and, if necessary, heated mildly or to the boiling temperature, until completion of the reaction. If the complex is insoluble in the reaction solvent, it can be filtered. If it is soluble, it can be recovered by evaporating off the solvent to a residue, for example through spray drying.

In case the resulting complex still contains free acid groups, it is transformed into a neutral salt by reaction with an organic or inorganic base which forms physiologically compatible cations in solutions.

For the preparation of these neutral salts, a sufficient amount of the base can be added to the complexes containing free acid groups in aqueous solution or suspension to neutrality. The resulting solution can thus be conveniently evaporated or a suitable solvent can be added to crystallize the complex salt.

Preferred inorganic bases cations suitable for salifying the chelated complexes of the invention comprise in particular alkali or alkaline-earth metal ions such as potassium, sodium, calcium, magnesium, and the mixtures thereof. Particularly preferred is the sodium ion.

Preferred organic base cations suitable for the above mentioned purpose comprise, inter alia, those of primary, secondary and tertiary amines, such as ethanclamine, diethanolamine, morpholine, glucamine, N-methylglucamine, N,N-dimethylglucamine, N-methylalucamine being particularly preferred.

Preferred amino acid cations comprise, for example, those of taurine, glycine, lysine, arginine or ornithine.

An alternative to this process consists in preparing the injectable formulation without isolating the complex salt. In this case it is mandatory for the final solutions to contain no free metal ions, which are toxic for the body.

This can be checked by titration, for example, with colored indicators such as Xylenol Orange. A final purification step of the complex salt could also be envisaged.

In this type of process the chelating agent, the salt or the metal oxide, and any salifying bases, are reacted in the stoichiometric ratios in water for injections, then, after completion of the reaction, pyrogens are filtered off and the product is distributed in suitable containers and then thermally sterilised.

The injectable pharmaceutical formulations are typically prepared by dissolving the active ingredient, prepared as described above, and the excipients in water of suitable purity from the pharmacological point of view, so as to provide a pharmaceutical formulation suitable for the enteral or parenteral administration, in concentrations ranging from 0.01 to 1.0 molar. The resulting contrast agent is suitably sterilised.

The contrast agents are administered, depending on the diagnostic requirements, at a dose of 0.01–0.3 mmol/kg body weight.

In principle, the doses for the parenteral administration range from 0.001 to about 1.0 mmol/kg body weight. The preferred doses for the parenteral administration range from 0.01 to about 0.5 mmol/kg body weight.

The doses for the enteral administration range, in general, from 0.5 to about 10 mmol/kg, preferably from about 1.0 to about 10 mmol/kg body weight.

The novel formulations of the present invention show good tolerability; moreover their water solubility is a further, important feature which makes them particularly suitable for use in nuclear magnetic resonance.

The diagnostic compositions of the present invention are used conventionally. The compositions can be administered to a patient, typically a hot-blooded animal, both systemically and topically in the organ or in the tissue to be visualized by magnetic resonance.

The analysis protocols and the apparatuses can be found in works such as Stark, D. D., Bradley, W. G., Magnetic Resonance Imaging, Mosby Year Book, St. Louis, Mo., 1992.

The experimental conditions used will be illustrated in detail in the Experimental section.

EXPERIMENTAL SECTION

EXAMPLE 1

Gadolinium Complex of [3β(S),5β]-3-[[4-[bis[2-[bis(carboxymethyl)amino]ethyl]amino]-4-carboxy-1-oxobutyl]amino]cholan-24-oic acid salified with 1-deoxy-1-(methylamino)-D-glucitol (1:3)

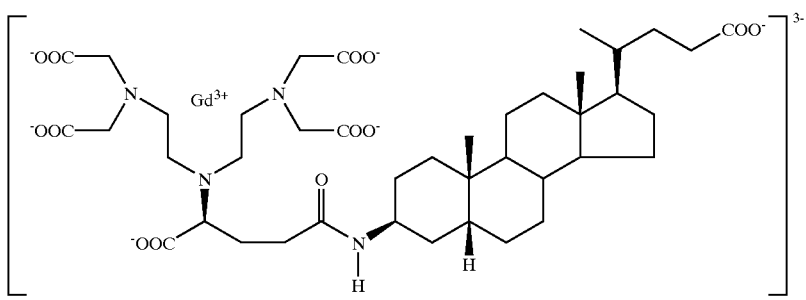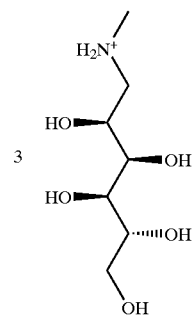

A) [3β(S),5β]-3-[[5-(1,1-Dimethylethoxy)-4-[bis[2-[bis[2-(1,1-dimethylethoxy)-2-oxoethyl]amino]ethyl]amino]-1,5-dioxopentyl]amino]cholan-24-oic acid methyl ester 3.6 g of [3β,5β]-3-aminocholan-24-oic acid methyl ester (prepared analogously to the procedure described in WO-A-95/32741: example 5) (9.24 mmol), 8.5 g of N,N-bis[2-[bis[2-(1,1-dimethylethoxy)-2-oxoethyl]amino]ethyl]-L-glutamic acid t-butyl ester (prepared as described in WO-A-95/32741: example 15) (11.39 mmol) and 1.64 g of diethyl cyanophosphonate (9.39 mmol; 1.55 mL) are dissolved in 160 mL of DMF. The solution is cooled to 0° C., 1.28 mL of $Et_3N$ (0.93 g; 9.24 mmol) are dropped therein and the reaction mixture is left for 30 min. at room temperature. After 1 h the solution is evaporated under reduced pressure, the residue is taken up in AcOEt, washed with 5% $NaHCO_3$ and then with brine. The organic phase is separated, dried over $Na_2SO_4$ and then evaporated under reduced pressure. The crude is purified by flash chromatography to obtain 9.5 g of the desired product (8.50 mmol).

Yield: 92%
K.F.: 3.47% (w/w)

| Elementary analysis | C | H | N |
|---|---|---|---|
| % calc.: | 66.63 | 9.74 | 5.01 |
| % found: | 67.42 | 10.08 | 5.07 |

TLC: Stationary phase: silica gel plate 60F 254 Merck
Eluent: AcOEt/n-hexane=4:6
Detection: 0.5% $KMnO_4$ in 1 M NaOH $R_f$=0.46
The $^1$H-NMR, $^{13}$C-NMR, IR and MS spectra are consistent with the indicated structure.

B) [3β(S),5β]-3-[[4-Carboxy-4-[bis[2-[bis(carboxymethyl)amino]ethyl]amino]-1-oxobutyl]amino]cholan-24-oic acid methyl ester A stirred solution of 9.3 g of the compound prepared at step A) (8.32 mmol) in 50 mL of $CH_2Cl_2$ is added with 5.1 mL of $CF_3COOH$ (7.6 g, 66.6 mmol;) after 10 min at a temperature of 0–5° C. the solution is evaporated. The residue is taken up into 50 mL of $CF_3COOH$ and, after 24 h at room temperature, added with a further 30 mL of $CF_3COOH$ to complete the reaction. After 5 h the reaction mixture is evaporated and the residue is treated with $CH_2Cl_2$, evaporating each time the solvent under reduced pressure until obtaining a powder. The solid is washed with $H_2O$, filtered and dried to obtain the desired product (6.9 g; 8.24 mmol).

Yield: 99% m.p.: 205° C.
K.F.: 7.78% (w/w)

| Elementary analysis | C | H | N |
|---|---|---|---|
| % calc.: | 60.27 | 8.18 | 6.69 |
| % found: | 59.28 | 8.11 | 6.68 |

TLC: Stationary phase: silica gel plate 60F 254 Merck
Eluent: $CHCl_3$/MeOH/25% $NH_4OH$=6:4:1
Detection: 0.5% $KMnO_4$ in 1 M NaOH $R_f$=0.28
The $^1$H-NMR, $^{13}$C-NMR, IR and MS spectra are consistent with the indicated structure.

C) [3β(S),5β]-3-[[4-[bis[2-[bis(Carboxymethyl)amino]ethyl]amino]-4-carboxy-1-oxobutyl]amino]cholan-24-oic acid A suspension of 6.14 g of the compound prepared at step B) (7.33 mmol) in 50 mL of $H_2O$ is added with 50 mL of 1 M NaOH (50 mmol) keeping pH 13 by means of a pH-stat apparatus. After 2 h at room temperature the reaction mixture is acidified (pH 0.5) with 12 N HCl to give a suspension which is filtered, washed With $H_2O$ and dried to give the desired product (5.64 g; 6.85 mmol).

Yield: 93% m.p.: 205° C.
K.F.: 9.02% (w/w)

| Elementary analysis | C | H | N | Cl | Na |
|---|---|---|---|---|---|
| % calc.: | 59.84 | 8.08 | 6.81 | | |
| % found: | 59.56 | 8.15 | 6.80 | <0.1 | <0.1 |

TLC: Stationary phase: silica gel plate 60F 254 Merck
Eluent: $CHCl_3$/MeOH/25% $NH_4OH$=6:4:1
Detection: 0.5% $KMnO_4$ in 1 M NaOH $R_f$=0.25
The $^1$H-NMR, $^{13}$C-NMR, IR and MS spectra are consistent with the indicated structure.

D) Gadolinium Complex of [3β(S),5β]-3-[[4-[bis[2-[bis(carboxymethyl)amino]ethyl]amino]-4-carboxy-1-oxobutyl]amino]cholan-24-oic acid salified with 1-deoxy-1-(methylamino)-D-glucitol (1:3), 4.53 g of the compound prepared at step C) (5.5 mmol) are suspended in 50 mL of H$_2$O and solubilised with 10 mL of a 2 M meglumine aqueous solution (20 mmol) having pH 6.8. After that, 11 mL of a 0.5 M GdCl$_3$ aqueous solution (5.5 mmol) are added in 1 h, keeping pH 6.8 by addition of 6.5 mL of a 2 M meglumine aqueous solution (13 mmol). The progress of the reaction is checked by capillary electrophoresis. After 2 h the solution is filtered through a Millipore® filter, nanofiltered and evaporated. The residue is dried to give the desired compound (6.15 g; 4.17 mmol).

Yield: 76% m.p.: 220° C.
K.F.: 8.44% (w/w)
CE assay: 100% (in % area)
Capillary:
fused silica 0.56 m×50 mm with a bulb cell
Voltage: 25 kV
Buffer: 0.05 M borate pH 9.3, 0.3 mM EDTA
Temperature: 40° C.

Stop time: 20 min
Detection (UV): 200–210 nm
Injection: hydrostatic (50 mbar, 5 s)
Concentration sample: 1 mg mL$^{-1}$;
Instrumentation: Hewlett PacKard 3D HPCE

| Preconditioning: | t (min) | action |
|---|---|---|
| | 2 | washing with H$_2$O |
| | 2 | washing with 0.1M NaOH |
| | 1 | washing with H$_2$O |
| | 5 | washing with buffer |
| | 9 | start analysis |

| Elementary analysis | C | H | Gd | N | Cl | Na |
|---|---|---|---|---|---|---|
| % calc.: | 47.65 | 7.35 | 10.06 | 6.27 | | |
| % found: | 47.83 | 7.36 | 10.01 | 6.24 | <0.1 | <0.1 |

The IR and MS spectra are consistent with the indicated structure.

The following compounds and the related gadolinium complexes are prepared analogously:

Gadolinium complex of [3β(S),5β,7α]-3-[[4-[bis[2-[bis(carboxymethyl)amino]ethyl]amino]-4-carboxy-1-oxobutyl]amino]-7-hydroxycholan-24-oic acid salified with 1-deoxy-1-(methylamino)-D-glucitol (1:3);

Gadolinium complex of [3β(S),5β,12α]-3-[[4-[bis[2-[bis(carboxymethyl)amino]ethyl]amino]-4-carboxy-1-oxobutyl]amino]-12-hydroxycholan-24-oic acid salified with 1-deoxy-1-(methylamino)-D-glucitol (1:3);

Gadolinium complex of [3α(S),5β]-3-[2[-[5-[bis[2-[bis(carboxymethyl)amino]ethyl]amino]-5-carboxypentyl]amino]-2-oxoethoxy]cholan-24-oic acid salified with 1-deoxy-1-(methylamino)-D-glucitol (1:3).

EXAMPLE 2

Gadolinium Complex of [3β(S),5β]-3-[[4-[bis[2-[bis(carboxymethyl)amino]ethyl]amino]-4-carboxy-1-oxobutyl]amino]-12-oxocholan-24-oic acid salified with 1-deoxy-1-(methylamino)-D-glucitol (1:3)

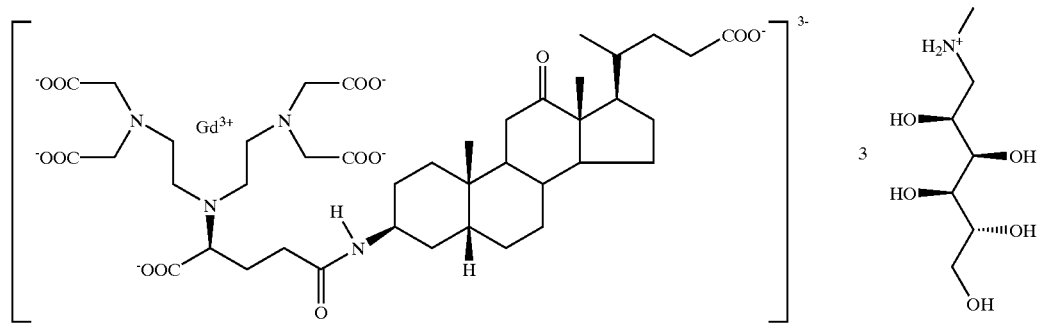

A) (3β,5β)-3-Azido-12-oxocholan-24-oic acid methyl ester 12.5 mL of Jones reagent (33.3 mmol Cr(VI)) are dropped into a solution of 17.8 g of (3β,5β,12α)-3-azido-12-hydroxycholan-24-oic acid methyl ester (41.1 mmol) (prepared analogously to the method described for (3β,5β,7α,12α)-3-azido-7,12-dihydroxycholan-24-oic acid methyl ester in WO-A-95/32741: example 5) in acetone (600 mL) in 90 min at room temperature. After 20 h the mixture is filtered and the solution is evaporated. The residue is dissolved in CHCl$_3$ (400 mL) and the solution is washed with a NaHCO$_3$ saturated aqueous solution then with H$_2$O. The solution is dried and evaporated to give a crude which is crystallized from 96% EtOH to obtain 14.1 g of the desired product (32.9 mmol).

Yield: 84% m.p.: 153° C.
K.F.:<0.1% (w/w)
$[\alpha]_D^{20}$=+83.25 (c 2.1. CHCl$_3$)

| Elementary analysis | C | H | N |
|---|---|---|---|
| % calc.: | 69.90 | 9.15 | 9.78 |
| % found: | 69.98 | 9.32 | 9.69 |

TLC: Stationary phase: silica gel plate 60F 254 Merck

Eluent: 8:2=n-hexane/AcOEt

Detection: 0.5% $KMnO_4$ in 1 M NaOH $R_f$=0.43

The $^1$H-NMR, $^{13}$C-NMR, IR and MS spectra are consistent with the indicated structure.

B) (3β,5β)-3-Amino-12-oxocholan-24-oic acid methyl ester

A solution of 16.4 g of compound A) (38.2 mmol) in THF (130 mL) is hydrogenated in the presence of Pd/C (1.6 g) at room temperature and at 40 bars for 15 h in an autoclave Parr®. The reaction mixture is filtered (paper and membrane FH 0.5 μm Millipore® and evaporated. The crude is purified by flash chromatography to give 11.8 g of the desired product (29.2 mmol).

Yield: 77% m.p.: 129–130° C.

K.F.: 1.04% (w/w)

$[\alpha]_D^{20}$=+87.8 (c 2.02, $CHCl_3$)

| Elementary analysis | C | H | N |
|---|---|---|---|
| % calc.: | 74.40 | 10.24 | 3.47 |
| % found: | 72.72 | 10.00 | 3.35 |

TLC: Stationary phase: silica gel plate 60F 254 Merck

Eluent: 95:5=MeOH/$Et_3$N

Detection: 0.5% $KMnO_4$ in 1 M NaOH $R_f$=0.31

The $^1$H-NMR, $^{13}$C-NMR, IR and MS spectra are consistent with the indicated structure.

C) [3β(S),5β]-3-[[4-[bis[2-[bis[2-(1,1-Dimethylethoxy)-2-oxoethyl]amino]ethyl]amino]-5(1,1-dimethylethoxy)-1,5-dioxopentyl]amino]-12-oxocholan-24-oic acid methyl ester A solution of DCC (6.24 g; 30.3 mmol) in $CH_2Cl_2$ (25 mL) is dropped in 30 min into a solution of N,N-bis[2-[bis[2-(1,1-dimethylethoxy)-2-oxoethyl]amino]ethyl]-L-glutamic acid 1-(1,1-dimethylethyl) ester (prepared as described in WO-A-95/32741: example 15) (21.5 g; 28.9 mmol), compound B) (11.1 g; 27.5 mmol) and HOBT (1-hydroxybenzotriazole) (3.72 g; 27.5 mmol) in $CH_2Cl_2$ (300 mL) at 0° C. under nitrogen. The mixture is left to warm to room temperature. After 21 h the reaction mixture is filtered and the solution is washed with a $NaHCO_3$ saturated aqueous solution, then $H_2O$, and subsequently evaporated. The crude is purified by flash chromatography to give 24.5 g of the desired product (21.7 mmol).

Yield: 79% m.p.: 205° C.

K.F.: 9.02% (w/w)

$[\alpha]_D^{20}$=+12.17 (c 2.07, $CHCl_3$)

TLC: Stationary phase: silica gel plate 60F 254 Merck

Eluent: 1:1=AcOEt/n-hexane

Detection: 0.5% $KMnO_4$ in 1 M NaOH $R_f$=0.45

The $^1$H-NMR, $^{13}$C-NMR, IR and MS spectra are consistent with the indicated structure.

D) [3β(S),5β]-3-[[4-[bis[2-[bis(Carboxymethyl)amino]ethyl]amino]-4-carboxy-1-oxobutyl]amino]-12-oxocholan-24-oic acid 80 mL of TFA (1.0 mol) are dropped into a solution of 23.8 g of the compound prepared at step C) (21.0 mmol) in $CH_2Cl_2$ (50 mL) at 0° C., in 1 h. The reaction mixture is cooled to room temperature then, after 2 h, evaporated. The residue is taken up in TFA (100 mL; 1.3 mol) and the solution stirred for a further 24 h. The reaction mixture is then evaporated, taken up in $CH_2Cl_2$ and evaporated again. The crude is dissolved in 150 mL of 1 M NaOH, cooling with an ice-bath, and the solution is stirred for 15 h (pH 10) at room temperature. The reaction mixture is adjusted to pH 13 with 3.30 mL of 30% NaOH and, after 4 h, filtered through a Millipore® filter (HAS 0.45 μm). The filtrate is slightly acidified with 12.5 mL of 30% HCl and 19 mL of 1 M HCl to pH 1.60. The precipitate is filtered, washed with $H_2O$ and dried to give 15.8 g of the desired product (18.9 mmol).

Yield: 90% m.p.: 172–175° C.

K.F.: 1.98% (w/w)

$[\alpha]_D^{20}$=+43.54 (c 2.02, 1 M NaOH)

HPLC: 97% (% area)

Stationary phase: Zorbax ECLIPSE XDB-C8 3.5 μm;150×4.6 mm.;

Temperature: 40° C.;

Mobile phase: gradient elution;

A=0.017 M $H_3PO_4$, 0.3 mM EDTA in water;

B=$CH_3$CN

| Gradient: | min | % A | % B |
|---|---|---|---|
| | 0 | 85 | 15 |
| | 40 | 65 | 35 |
| | 50 | 65 | 35 |

Flow rate: 1.5 mL $min^{-1}$;

Detection (UV): 210 nm;

| Elementary analysis | C | H | N | Cl | Na |
|---|---|---|---|---|---|
| % calc.: | 58.84 | 7.71 | 6.69 | | |
| % found: | 56.57 | 7.68 | 6.37 | 0.25 | 0.18 |

TLC: Stationary phase: silica gel plate 60F 254 Merck

Eluent: 5:4:2=$CHCl_3$/MeOH/25% $NH_4$OH

Detection: 0.5% $KMnO_4$ in 1 M NaOH $R_f$=0.28

The $^1$H-NMR, $^{13}$C-NMR, IR and MS spectra are consistent with the indicated structure.

E) Gadolinium Complex of [3β(S),5β]-3-[[4-[bis[2-[bis(carboxymethyl)amino]ethyl]amino]-4-carboxy-1-oxobutyl]amino]-12-oxocholan-24-oic acid salified with 1-deoxy-1-(methylamino)-D-glucitol (1:3)

49.0 mL of a 0.918 M meglumine aqueous solution (45.0 mmol) are dropped into a suspension of 14.0 g of the compound prepared at step D) (16.7 mmol) in $H_2O$ (100 mL), at room temperature, to give a clear solution (pH 6.5). 31.6 mL of a 0.503 M $GdCl_3$ aqueous solution (15.9 mmol) are dropped therein keeping pH 6.5 by addition of 55.7 mL of a 0.918 M meglumine aqueous solution (51.1 mmol) by means of a pH-stat. At the end of the additions the mixture is filtered through a Millipore® filter (HAWP 0.45 μm), nanofiltered, adjusted to pH 7.0 with 0.100 mL of a 0.918 M meglumine aqueous solution (0.092 mmol) and evaporated. The residue is dried ($P_2O_5$, 50° C.) to give 22.0 g of the desired product (14.0 mmol).

Yield: 84% m.p.: 100–105° C.
K.F.: 5.06% (w/w)
HPLC assay: 97% (% area)
Stationary phase: HYPURITY™ Elite C18 5 μm; 250× 4.6 mm column of Hypersil;
Temperature: 40° C.;
Mobile phase:
gradient elution;
A=0.01 M $KH_2PO_4$ in water;
B=$CH_3CN$

| Gradient: | min | % A | % B |
|---|---|---|---|
| | 0 | 95 | 5 |
| | 40 | 65 | 35 |
| | 50 | 65 | 35 |

Flow rate: 1 mL min$^{-1}$;
Detection (UV): 210 nm;

| Elementary analysis | C | H | N | Gd | Na | Cl |
|---|---|---|---|---|---|---|
| % calc.: | 47.23 | 7.16 | 6.22 | 9.97 | | |
| % found: | 45.70 | 7.32 | 6.00 | 9.41 | <0.1 | <0.1 |

The IR and MS spectra are consistent with the indicated structure.

EXAMPLE 3

Gadolinium Complex of (3β,5β,7α,12α)-3-[[[bis[2-[bis(carboxymethyl)amino]ethyl]amino]acetyl] amino]-7,12-dihydroxycholan-24-cic acid Salified with 1-deoxy-1-(methylamino)-D-glucitol (1:2)

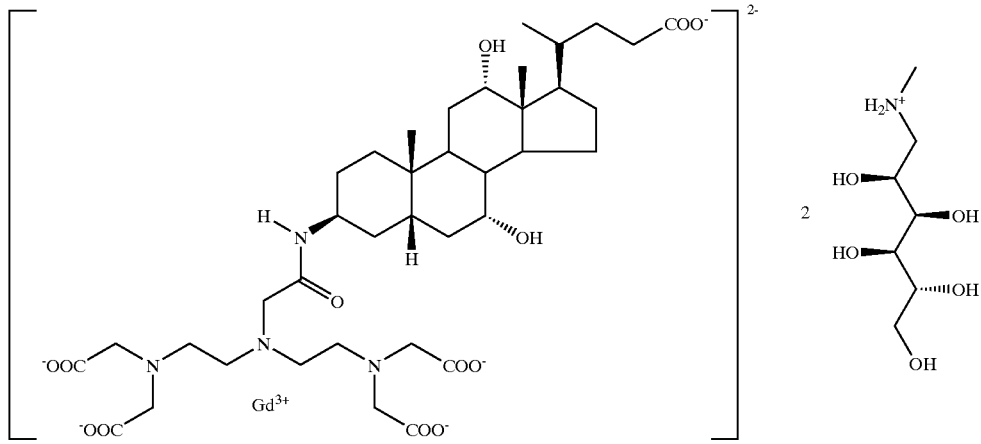

A) (3β,5β,7α,12α)-3-[[[bis[2-[bis[2-(1,1-Dimethylethoxy)-2-oxoethyl]amino]ethyl]amino] acetyl]amino]-7,12-dihydroxycholan-24-oic acid methyl ester 24.8 g of (3β,5β,7α,12α)-3-[(aminoacetyl)amino]-7,12-dihydroxycholan-24-oic acid methyl ester (prepared according to the procedure described in WO-A-95/32741: example 5) (51.9 mmol) are suspended in a stirred solution of 38.7 g of N-(2-bromoethyl)-N-[2-(1,1-dimethylethoxy)-2-oxoethyl]glycine 1,1-dimethylethyl ester (prepared according to the procedure described in WO-A-95/32741: example 15) (110 mmol) in 390 mL of $CH_3CN$. The addition of 245 mL of 2 M buffer phosphate pH 8 gives a biphasic solution which is vigorously stirred at room temperature for 144 h. The organic phase is separated and evaporated and the residual oil is dissolved in 250 mL of $CH_2Cl_2$. The solution is washed with $H_2O$, dried ($Na_2SO_4$) and evaporated.

The crude is purified by flash chromatography (eluent $CHCl_3/CH_3OH$=95:5) to give the desired product (24.8 g; 24.3 mmol).

Yield: 47%
$[\alpha]_D^{20}$=+9.45 (c 1.5, $CHCl_3$)

| Elementary analysis | C | H | N |
|---|---|---|---|
| % calc.: | 64.68 | 9.47 | 5.49 |
| % found: | 64.55 | 9.44 | 5.46 |

TLC: Stationary phase: silica gel plate 60F 254 Merck
Eluent: $CHCl_3$/MeOH=88:12
Detection: 0.5% $KMnO_4$ in 1 M NaOH $R_f$=0.57
The $^1$H-NMR, $^{13}$C-NMR, IR and MS spectra are consistent with the indicated structure.

B) (3β,5β,7α,12α)-3-[[[bis[2-[bis(Carboxymethyl) amino]ethyl]amino]acetyl]amino]-7,12-dihydroxycholan-24-oic acid 318 mL of a 2 M LiOH aqueous solution (636 mmol) are added dropwise, in 15 min, to a solution of the compound prepared at step A) (21.6 g; 21.1 mmol) in 310 mL of EtOH. After 23 h EtOH is evaporated off and the reaction mixture is stirred for a further 2 h. The solution is dropped into 255 mL of 2.6 M HCl and pH is adjusted to 1.4 with 30% NaOH. After 1.5 h the precipitate is filtered, washed with 300 mL of 0.1 M HCl and dried to give the desired product (13.1 g; 16.7 mmol).

Yield: 78% m.p.: 129–132° C. dec
HPLC assay: 97.8% (in % area)
Stationary phase: Lichrosorb RP-Select B 5 μm; 250×4 mm column Merck KGaA;
Temperature: 45° C.;

Mobile phase:

gradient elution;

A=0.01 M $KH_2PO_4$ and 0.017 M $H_3PO_4$ in water
B=$CH_3CN$

| min | % A | % B |
|---|---|---|
| 5 | 95 | 5 |
| 5 | 20 | 80 |
| 45 | 20 | 80 |

Flow rate: 1 mL min$^{-1}$;
Detection (UV): 210 nm;
Complexometric titre: 95.5% (0.1 M $GdCl_3$)% (w/w)
$[\alpha]_D^{20}$=+13.03 (c 5, 1 M NaOH)

| Elementary analysis | C | H | N | Cl | |
|---|---|---|---|---|---|
| % calc.: | 58.30 | 7.98 | 7.16 | | |
| % found: | 54.63 | 8.12 | 6.64 | 1.82 | $H_2O$ 4.89 | mL of $CH_3CN$ and 740 mL $H_2O$. The solution is buffered to pH 7 with $H_3PO_4$.

Flow rate: 1 mL min$^{-1}$;

Detection (UV): 210 nm;

| Elementary analysis | C | H | Gd | N | |
|---|---|---|---|---|---|
| % calc.: | 47.05 | 7.06 | 11.84 | 6.33 | |
| % found: | 45.19 | 7.21 | 11.22 | 6.07 | $H_2O$ 4.16 |

The IR and MS spectra are consistent with the indicated structure.

EXAMPLE 4

Gadolinium Complex with [3β(S),5β,12α]-3-[[4-[bis[2-[bis(carboxymethyl)amino]ethyl]amino]-4-carboxy-1-oxobutyl]amino]-12-hydroxycholan-24-oic acid Salified with 1-deoxy-1-(methylamino)-D-glucitol (1:3)

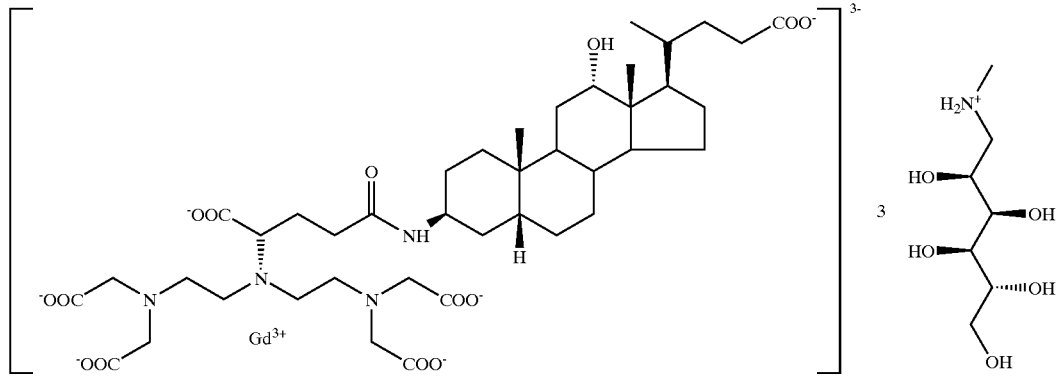

C) Gadolinium Complex of (3β,5β,7α,12α)-3-[[[bis[2-[bis(carboxymethyl)amino]ethyl]amino]acetyl]amino]-7,12-dihydroxycholan-24-oic acid Salified with 1-deoxy-1-(methylamino)-D-glucitol (1:2)

11.3 g of the compound prepared at step B) (13.8 mmol) are suspended in 40 mL of $H_2O$ and dissolved by addition of 44.7 mL of a 1 M meglumine aqueous solution (44.7 mmol) having pH 6. 13.7 mL of a 1 M $GdCl_3$ aqueous solution (13.7 mmol) are dropped into the mixture in 1 h keeping pH 6.5 by addition of 73.5 mL of a 1 M meglumine aqueous solution (73.5 mmol). The reaction mixture is nanofiltered and pH is adjusted to 6.8 with 0.3 mL of 0.1 M meglumine. After evaporation and drying the desired product is obtained (17.2 g; 12.9 mmol).

Yield: 93% m.p.: 245–249° C. dec.

Free ligand: <0.1% (0.001 M $GdCl_3$)

HPLC assay: 100% (in % area)

Stationary phase: Lichrospher 100 RP-8 5μ; 250×4 mm column Merck KGaA;

Temperature: 40° C.;

Mobile phase: isocratic elution with premixed phase: 1 g of n-octylamine and 0.3 mmol of $Na_2EDTA$ are added to 260

A) [3β(S),5β,12α]-3-[[4-[bis[2-[bis[2-(1,1-Dimethylethoxy)-2-oxoethyl]amino]ethyl]amino]-5-(1,1-dimethylethoxy)-1,5-dioxopentyl]amino]-12-hydroxycholan-24-oic acid methyl ester Triethylamine (2.23 g; 22 mmol) is added to a solution of 8.93 g of [3β,5β,12α]-3-amino-12-hydroxycholan-24-oic acid methyl ester (prepared analogously to the cholic acid derivative described in WO-A-95/32741: example 5) (22 mmol), 16.41 g of N,N-bis[2-[bis[2-(1,1-dimethylethoxy)-2-oxoethyl]amino]ethyl]-L-glutamic acid 1-(1,1-dimethylethyl) ester (prepared as described in WO-A-95/32741: example 15) (22 mmol) and 3.91 g of diethyl cyanophosphonate (24 mmol) in 300 mL of DMF at 0° C. After 1.5 h at 0° C. and 18 h at room temperature, the reaction mixture is evaporated and the residue is dissolved in AcOEt. The solution is washed with a $NaHCO_3$ saturated solution and $H_2O$, dried ($Na_2SO_4$) and evaporated. The crude is purified by flash chromatography to give the desired product (20.67 g; 18.2 mmol).

Yield: 83%

$[\alpha]_D^{20}$=−6.75 (c 2.0, CHCl$_3$)

| Elementary analysis | C | H | N |
|---|---|---|---|
| % calc.: | 65.69 | 9.60 | 4.94 |
| % found: | 66.54 | 9.95 | 4.99 |

TLC: Stationary phase: silica gel plate 60F 254 Merck

Eluent: n-hexane/AcOEt=1:1 R$_f$=0.09

Detection: Ce(SO$_4$)$_2$, 4 H$_2$O (0.18%) and (NH$_4$)$_6$Mo$_7$O$_{24}$.4 H$_2$O (3.83%) in 10% H$_2$SO$_4$ The $^1$H-NMR, $^{13}$C-NMR, IR and MS spectra are consistent with the indicated structure.

B) [3β(S),5β,12α]-3-[[4-[bis[2-[bis(Carboxymethyl)amino]ethyl]amino]-4-carboxy-1-oxobutyl]amino]-12-hydroxycholan-24-oic acid The compound prepared at step A) (19.72 g; 17.4 mmol) is dissolved in 105 mL CF$_3$CO$_2$H at room temperature. After 26 h the solution is evaporated and the residue is treated with H$_2$O; the solid is filtered, washed with H$_2$O and partially dried under vacuum.

The resulting intermediate is dissolved in H$_2$O to pH 13 with 1 M NaOH.

After 5 h at room temperature 0.5 M HCl is dropped into the solution to pH 1.4. After 15 h at room temperature the precipitate is filtered, washed with H$_2$O and dried under vacuum to give a crude which is purified by chromatography over resin Amberlite® XAD 1600 to obtain the desired product (9.92 g; 11.8 mmol).

Yield: 68% m.p.: 184° C. (dec.)

Complexometric titre (0.1 M GdCl$_3$): 99.3% (w/w)

Acidic titer (0.1 N NaOH): 99.8% (w/w)

$[\alpha]_D^{20}$ (C 2.0; 1 M NaOH)

| λ(nm) | 589 | 578 | 546 | 436 | 405 | 365 |
|---|---|---|---|---|---|---|
| [α] | +23.61 | +24.59 | +27.90 | +46.67 | +55.61 | +71.40 |

| Elementary analysis | C | H | N | |
|---|---|---|---|---|
| % calc.: | 58.70 | 7.93 | 6.68 | |
| % found: | 58.22 | 8.16 | 6.59 | H$_2$O 0.70% |

TLC: Stationary phase: silica gel plate 60F 254 Merck

Eluent: CHCl$_3$/MeOH/NH$_4$OH=5:4:2 R$_f$=0.13

Detection: Ce(SO$_4$)$_2$.4 H$_2$O (0.18%) and (NH$_4$)$_6$Mo$_7$O$_{24}$.4 H$_2$O (3.83%) in 10% H$_2$SO$_4$ The $^1$H-NMR, $^{13}$C-NMR, IR and MS spectra are consistent with the indicated structure.

C) Gadolinium Complex of [3β(S),5β,12α]-3-[[4-[bis[-2-[bis(carboxymethyl)amino]ethyl]amino]-4-carboxy-1-oxobutyl]amino]-12-hydroxycholan-24-oic acid Salified with 1-deoxy-1-(methylamino)-D-glucitol (1:3)

The compound prepared at step B) (8.39 g; 10 mmol) is suspended in H$_2$O (30 mL) and dissolved by addition of 1 M aqueous meglumine (36.5 mL; 36.5 mmol) to pH 6. A 1.025 M GdCl$_3$ aqueous solution (9.85 mL; 10.1 mmol) is added in 1 h keeping pH 6 by addition of 1 M aqueous meglumine (19.3 mL; 19.3 mmol). The solution is nanofiltered and pH is adjusted to 7.0 with 1 M aq. meglumine.

After evaporation and drying the desired product is obtained (8.57 g; 5.4 mmol).

Yield: 54% m.p.: 150–166° C. (170° C. dec.)

| Elementary analysis | C | H | N | Gd | |
|---|---|---|---|---|---|
| % calc.: | 47.17 | 7.28 | 6.21 | 9.96 | |
| % found: | 43.40 | 7.31 | 5.68 | 9.31 | H$_2$O 7.14% |

The IR and MS spectra are consistent with the indicated structure.

D) Analogously to the Compound Prepared at Step C), the gadolinium Complex of [3β(S),5β,12α]-3-([4-[bis[2-[bis(carboxymethyl)amino]ethyl]amino]-4-carboxy-1-oxobutyl]amino]-12-hydroxycholan-24-oic acid salified with sodium (1:3) is Prepared The compound prepared at step B) (26.92 g; 32.08 mmol) is suspended in H$_2$O (100 mL) and dissolved by addition of 2 M NaOH (56 mL; 112 mmol) to pH 6. A 0.512 M GdCl$_3$ aqueous solution (58.2 mL; 29.77 mmol) is added in 3 h keeping pH 6 by addition of 2 M NaOH (28.95 mL; 57.9 mmol). The pH of the solution is adjusted to 6.7 with 2 M NaOH (4 mL; 8 mmol) and the solution is nanofiltered.

After freeze-drying, the desired product is obtained (29.86 g; 28.2 mmol).

Yield: 88% m.p.: >300° C.

| Elementary analysis | C | H | N | Gd | Na | |
|---|---|---|---|---|---|---|
| % calc.: | 46.49 | 5.71 | 5.29 | 14.85 | 6.51 | |
| % found: | 43.98 | 6.34 | 4.92 | 13.86 | 6.16 | H$_2$O 4.63% |

The IR and MS spectra are consistent with the indicated structure.

EXAMPLE 5

Alternative Method for the Preparation of [3β(S),5β,12α]-3-[[4-[bis[2-[bis(carboxymethyl)amino]ethyl]amino]-4-carboxy-1-oxobutyl]amino]-12-hydroxycholan-24-oic acid According to Scheme 3

A) (S)-5-oxo-1,2-pyrrolidinedicarboxylic acid 2-methyl 1-(phenylmethyl)diester 7.1 g of CH$_3$I (50 mmol) are added to a solution of 6.58 g of (S)-5-oxo-1,2-pyrrolidinedicarboxylic acid 1-(phenylmethyl)ester (25 mmol) and N,N-diisopropylethylamine (3.55 g; 27.5 mmol) in CH$_2$Cl$_2$ (33 mL) and the reaction mixture is refluxed for 6.5 h. After cooling at room temperature, the reaction mixture is diluted with CH$_2$Cl$_2$ (50 mL); the organic phase is washed with H$_2$O, 2% aq. Na$_2$CO$_3$, 0.2 N HCl and H$_2$O, dried over Na$_2$SO$_4$ and evaporated to give the desired product (6.8 g; 24.5 mmol).

Yield: 98%

HPLC assay: 98.5% (in % area)

Stationary phase: Lichrosorb RP-Select B 5 μm; 250×4 mm column Merck KGaA;

Temperature: 45° C.;

Mobile phase:

gradient elution;
A=0.017 M $H_3PO_4$ in water
B=$CH_3CN$

| | Gradient: | |
|---|---|---|
| min | % A | % B |
| 0 | 80 | 20 |
| 15 | 80 | 20 |
| 35 | 40 | 60 |

Flow rate: 1 mL min$^{-1}$;
Detection (UV): 210 nm.
$[\alpha]_\lambda^{20}$ (C 2; $CHCl_3$)

| λ(nm) | 589 | 578 | 546 | 365 |
|---|---|---|---|---|
| $[\alpha]_\lambda^{20}$ | −42.97 | −44.79 | −50.09 | −100.43 |
| Elementary analysis | C | H | N | |
| % calc.: | 60.64 | 5.45 | 5.05 | |
| % found: | 60.94 | 5.54 | 5.00 | |

The $^1$H-NMR, $^{13}$C-NMR, IR and MS spectra are consistent with the indicated structure.

B) [3β(S),5β,12α]-3-[[5-Methoxy-1,5-dioxo-4-[[(phenylmethoxy)carbonyl]amino]pentyl]amino]-12-hydroxycholan-24-oic acid methyl ester 8.92 g of [3β,5β,12α]-3-amino-12-hydroxycholan-24-oic acid methyl ester (prepared analogously to the cholic acid derivative described in WO-A-95/32741: example 5) (22 mmol) is added to a solution of compound A) (6.1 g; 22 mmol) in dioxane (55 mL) and the resulting mixture is heated at 50° C. for 24 h and then at 105° C. for 29 h. The solvent is evaporated off under reduced pressure and the residue is purified by flash chromatography (gradient elution AcOEt/hexane) followed by crystallization with the mixture AcOEt/hexane=1/1, to give the desired product (11.2 g; 16.4 mmol).

Yield: 75% m.p.: 140° C.
HPLC assay: 99.2% (in % area)
Stationary phase: Lichrosorb RP-Select B 5 μm; 250×4 mm column Merck KGaA;
Temperature: 45° C.;
Mobile phase:
gradient elution;
A=0.017 M $H_3PO_4$ in water
B=$CH_3CN$

| | Gradient: | |
|---|---|---|
| min | % A | % B |
| 0 | 65 | 35 |
| 25 | 15 | 85 |
| 30 | 15 | 85 |

Flow rate: 1 mL min$^{-1}$;
Detection (UV): 210 nm.
$[\alpha]_\lambda^{20}$ (c 2.01; $CHCl_3$)

| λ(nm) | 589 | 578 | 546 | 365 |
|---|---|---|---|---|
| $[\alpha]_\lambda^{20}$ | +24.14 | +25.13 | +28.51 | +73.81 |
| Elementary analysis | C | H | N | |
| % calc.: | 68.70 | 8.43 | 4.11 | |
| % found: | 69.36 | 8.72 | 4.13 | |

TLC: Stationary phase: silica gel plate 60F 254 Merck
Eluent: AcOEt
Detection: $Ce(SO_4)_2$ 4 $H_2O$ (0.2%) and $(NH_4)_6Mo_7O_{24}$ 4 $H_2O$ (3.8%) in 10%$H_2SO_4$ $R_f$=0.11
The $^1$H-NMR, $^{13}$C-NMR, IR and MS spectra are consistent with the indicated structure.

C) [3β(S),5β,12α]-3-[[4-[bis[2-[bis[2-(1,1-Dimethylethoxy)-2-oxoethyl]amino]ethyl]amino]-5-methoxy-1,5-dioxopentyl]amino]-12-hydroxycholan-24-oic acid methyl ester 1 g of 5% Pd/C is added to a solution of compound B) (10.4 g; 15.3 mmol) in MeOH (100 mL); the suspension is stirred for 3.5 h under hydrogen atmosphere (absorbed $H_2$: 348 mL; 15.5 mmol) at room temperature. After filtration over a Millipore® FH filter (0.45 μm), the solution is evaporated under reduced pressure to give a residue which is dissolved in $CH_3CN$ (60 mL). 2 M Aqueous phosphate buffer pH 8 (60 mL) is added, then a solution of N-(2-bromoethyl)-N-[2-(1,1-dimethylethoxy)-2-oxoethyl]glycine 1,1-dimethylethyl ester (prepared according to the procedure described in WO-A-95/32741: example 15) (11.86 g; 33.7 mmol) in $CH_3CN$ (15 mL) is added dropwise in 10 min at room temperature. The mixture is stirred for 39 h. After separation, the organic phase is evaporated under reduced pressure and the residue is dissolved in AcOEt (200 mL). The solution is washed with $H_2O$, dried ($Na_2SO_4$) and evaporated under reduced pressure. The crude is purified by flash chromatography (gradient elution AcOEt/hexane) to give the desired product (11.36 g; 10.4 mmol).

Yield: 68% m.p.: 55–58° C.
HPLC assay: 100% (in % area)
$[\alpha]_\lambda^{20}$ (c 2.01; $CHCl_3$)

| λ(nm) | 589 | 578 | 546 | 365 |
|---|---|---|---|---|
| $[\alpha]_\lambda^{20}$ | −6.97 | −7.41 | −8.61 | −32.89 |
| Elementary analysis | C | H | N | |
| % calc.: | 64.93 | 9.42 | 5.13 | |
| % found: | 65.06 | 9.36 | 5.11 | |

TLC: Stationary phase: silica gel plate 60F 254 Merck
Eluent: AcOEt
Detection: $Ce(SO_4)_2$ 4 $H_2O$ (0.2%) and $(NH_4)_6Mo_7O_{24}$ 4 $H_2O$ (3.8%) in 10% $H_2SO_4$ $R_f$=0.45
The $^1$H-NMR, $^{13}$C-NMR, IR and MS spectra are consistent with the indicated structure.

D) [3β(S),5β,12α]-3-[4-[bis[2-[bis(Carboxymethyl)amino]ethyl]amino]-4-carboxy-1-oxobutyl]amino]-12-hydroxycholan-24-oic acid A solution of compound C) (8.5 g; 7.8 mmol) in dioxane (50 mL) is added with a 2 M LiOH aqueous solution (117 mL; 234 mmol). The resulting mixture is stirred at room temperature for 72 h and then acidified to pH 6 by slow addition of 37% HCl. The solution is concentrated to 50 g by evaporation under reduced pressure and diluted with $H_2O$ (40 mL). The solution is acidified to pH 2.5 by addition of 37% HCl, heated to 50–55° C. and, keeping under strong stirring, acidified very slowly to pH 1.3 with 2 N HCl. After 5 min the heterogeneous mixture is left to slowly cool at room temperature, under stirring, for 15 h. The precipitate is filtered off, washed with $H_2O$ and dried to give the desired product (5.92 g; 7 mmol).

EXAMPLE 6

Gadolinium Complex of (3β,5β,7α,12α)-3-[[[[[(bis[2-[bis(carboxymethyl)amino]ethyl]amino]acetyl]amino]acetyl]amino]-7,12-dihydroxycholan-24-oic acid Salified with 1-deoxy-1-(methylamino)-D-glucitol (1:2)

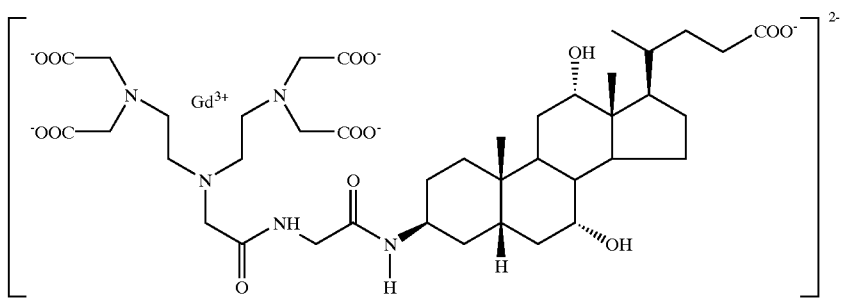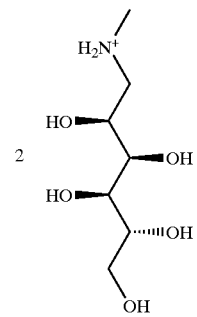

Yield: 90% m.p.: 180–198° C.

K.F.: 0.95% (w/w)

HPLC assay: 99.9% (in % area)

Stationary phase: Zorbax ECLIPSE XDB-C8 3.5 µm; 150×4.6 mm column Rockland Technologies, Inc.;

Temperature: 40° C.;

Mobile phase:

gradient elution;

A=0.017 M $H_3PO_4$, 0.3 mM EDTA in water;

B=$CH_3CN$

| Gradient: | min | % A | % B |
|---|---|---|---|
| | 0 | 85 | 15 |
| | 40 | 65 | 35 |
| | 50 | 65 | 35 |

Flow rate: 1.5 mL min$^{-1}$;

Detection (UV): 210 nm;

Acidic titer (0.1 N NaOH): 99% (w/w)

$[\alpha]_\lambda^{20}$ (c 2.04; 1 N NaOH)

| λ(nm) | 589 | 578 | 546 | 436 | 405 | 365 |
|---|---|---|---|---|---|---|
| $[\alpha]_\lambda^{20}$ | +24.80 | +25.83 | +29.22 | +49.02 | +58.43 | +75.59 |

| Elementary analysis | C | H | N | Cl | Li |
|---|---|---|---|---|---|
| % calc.: | 58.70 | 7.93 | 6.68 | | |
| % found: | 57.90 | 7.97 | 6.57 | <0.1 | <0.1 |

The $^1$H-NMR, $^{13}$C-NMR, IR and MS spectra are consistent with the indicated structure.

A) N-[[bis[2-[bis[2-(1,1-dimethylethoxy-2-oxoethyl]amino]ethyl]amino]acetyl]glycine 5 6.5 g of glycylglycine (49.3 mmol) are suspended in 100 mL of a 1:1=$H_2O$: EtOH mixture and dissolved at pH 10 with 10 M NaOH (4.8 mL). N-(2-bromoethyl)-N[2-(1,1-dimethylethoxy)-2-oxoethyl]glycine 1,1-dimethylethyl ester (42 g; 110.9 mmol) in 40 mL of EtOH is dropped therein in 2 h, keeping pH 10.5 with 10 M NaOH (5.8 mL). The solution rapidly turns into an emulsion, which is dissolved after 2.5 h by addition of 10 M NaOH. After 22 h the solvent is evaporated off, the mixture is diluted with water and extracted with $CH_2Cl_2$. The organic phase is washed with $H_2O$, dried and evaporated, to give a residue which is purified by flash chromatography. The residue is dissolved in water, pH is adjusted to 4.5 by addition of 1 M HCl and the solution is extracted with chloroform. The organic phase is washed with $H_2O$, dried and evaporated, to give 13 g of the desired product (19.3 mmol).

Yield: 39%

| Elementary analysis | C | H | N |
|---|---|---|---|
| % calc.: | 56.95 | 8.66 | 8.30 |
| % found: | 56.67 | 8.68 | 8.30 |

TLC: Stationary phase: silica gel plate 60F 254 Merck

Eluent: $CHCl_3$/MeOH/$NH_4OH$ 25%=6:3:1

$R_f$=0.65

Detection: $KMnO_4$ in alkaline solution

The $^1$H-NMR, $^{13}$C-NMR, IR and MS spectra are consistent with the indicated structure.

B) (3β,5β,7α,12α)-3-[[[[[bis[2-[bis[2-(1,1-Dimethylethoxy)-2-oxoethyl]amino]ethyl]amino]acetyl]amino]acetyl]amino]-7,12-dihydroxycholan-24-oic acid Methyl ester 2.8 mL of TEA (20.2 mmol) are dropwise added in 5 min. to a solution of 13.6 g of the compound prepared at step A)

(20.2 mmol), with 8.52 g of (3β,5β,7α,12α)-3-amino-7,12-dihydroxycholan-24-oic acid methyl ester (20.2 mmol) and DEPC (3.4 mL; 22.2 mmol) in DMF (290 mL) stirring at 0° C. After 1 h the reaction is warmed to room temperature and the solution is stirred for 6.5 h. 0.3 mL of DEPC (2 mmol) are added and the solution is stirred for a further 15.5 h. DMF is evaporated off, the residue is dissolved in AcOEt, washed with aq. NaHCO₃ and finally water and then dried. After purification by flash chromatography, 13.7 g of the desired product are obtained (12.7 mmol).

Yield: 63%

$[\alpha]_\lambda^{20} = +5.26$ (c 1.5; CHCl₃)

| Elementary analysis | C | H | N |
|---|---|---|---|
| % calc.: | 63.48 | 9.25 | 6.49 |
| % found: | 63.22 | 9.40 | 6.40 |

The ¹H-NMR, ¹³C-NMR, IR and MS spectra are consistent with the indicated structure.

C) (3β,5β,7α,12α)-3-[[[[[bis[2-[bis(Carboxymethyl)amino]ethyl]amino]acetyl]amino]acetyl]amino]-7,12-dihydroxycholan-24-oic acid 12.85 g of the compound prepared at step B) (12 mmol) are dissolved in TFA (210 mL) stirring at 0±50° C. After 16 h TFA is evaporated off to give a residue which is dissolved in 90 mL of 0.8 M NaOH at pH 13 and stirred at room temperature for 15 h. The solution is concentrated to 50 mL, dropped into 105 mL of 0.6 M HCl and stirred for 2 h. The solid is filtered, washed with 0.1 M HCl and dried to obtain a crude which is purified by chromatography. The fractions containing the desired compound in the salified form are evaporated to give a residue which is dissolved in water and dropped into 1 M HCl, pH 1.45. The precipitate is filtered, washed with 0.1 M HCl and dried to give 2.6 g of the desired product (3.1 mmol).

Yield: 26% m.p.: 120–125° C.

HPLC assay: 98% (% area)

The ¹H-NMR, ¹³C-NMR, IR and MS spectra are consistent with the indicated structure.

D) Gadolinium Complex of (3β,5β,7α,12α)-3-[[[[[bis[2-bis(carboxymethyl)amino]ethyl]amino]acetyl]amino]acetyl]amino]-7,12-di-hydroxycholan-24-oic acid Salified with 1-deoxy-1-(methylamino)-D-glucitol (1:2)

2.59 g of the compound prepared at step C) (3.08 mmol) are suspended in water and dissolved by addition of a 1 M meglumine aqueous solution (3.08 mL; 3.08 mmol) to pH 5. Gd₂O₃ (0.5015 g; 2.77 mmol) is added to the mixture heating to 50° C. After 1 h meglumine (2.8 mL; 2.8 mmol) is added to dissolve the precipitate. After 24 h the reaction mixture is filtered and pH is adjusted to 6.8 with 1 M aqueous meglumine (0.4 mL). After evaporation and drying, 4.2 g (3.00 mmol) of the desired product are obtained.

Yield: 99% m.p.: 209–213° C. dec.

HPLC assay: 99.7% (% area)

Free ligand: <0.1% (0.001 GdCl₃)

| Elementary analysis | C | H | N | Gd | |
|---|---|---|---|---|---|
| % calc.: | 46,84 | 6,99 | 7,08 | 11,36 | |
| % found: | 44,01 | 7,35 | 6,68 | 10,39 | H₂O 4,95 |

The IR and MS spectra are consistent with the indicated structure.

EXAMPLE 7

Gadolinium Complex of [3β(S),5β]-3-[[4-[bis[2-[bis(carboxymethyl)amino]ethyl]amino]-4-carboxy-1-oxobutyl](carboxymethyl)amino]cholan-24-oic acid Salified with 1-deoxy-1-(methylamino)-D-glucitol (1:4)

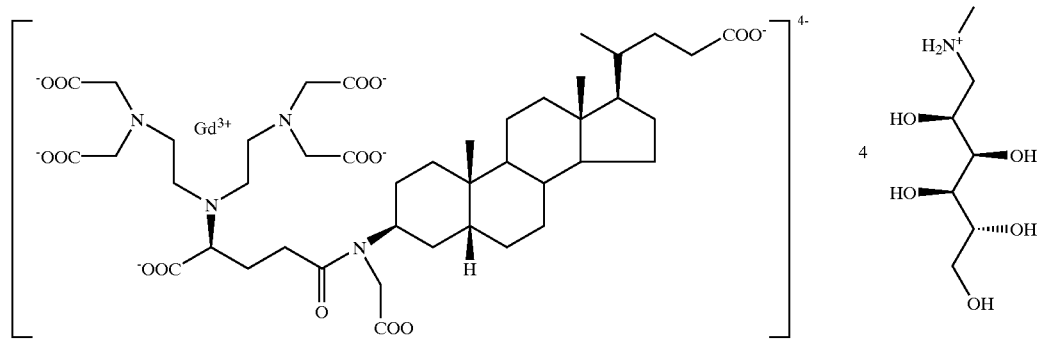

A) (3β,5β)-3-[[2-(1,1-Dimethylethoxy)-2-oxoethyl]aminolcholan-24-oic acid methyl ester 40.0 g of (3β,5β)-3-aminocholan-24-oic acid methyl ester (prepared as in Example 1 above) (103 mmol) are suspended in DMF (1.0 l) at room temperature under nitrogen. Triethylamine (13.0 g; 17.8 mL; 129 mmol) is added, then a solution of bromoacetic acid 1,1-dimethylethyl ester (24.0 g; 18.0 mL; 123 mmol) in DMF (30 mL) is dropped into the reaction mixture in 1 h until dissolution. After 3 days the mixture is concentrated and diluted in a 4% NaHCO₃ aqueous solution. The resulting suspension is filtered and the precipitate is washed with H₂O and dried to give 33.7 g of the desired product (66.9 mmol).

Yield: 65% m.p.: 62–64° C.

K.F.: <0.1%

$[\alpha]^{22}D = +23.55$ (c 1.96, MeOH)

| Elementary analysis | C | H | N |
|---|---|---|---|
| % calc.: | 73.91 | 10.60 | 2.78 |
| % found: | 74.67 | 10.85 | 2.78 |

TLC: Stationary phase: silica gel plate 60F 254 Merck
Eluent: 7:3=n-hexane/AcOEt $R_f$=0.31
The $^1$H-NMR, $^{13}$C-NMR, IR and MS spectra are consistent with the indicated structure.

B) [3β(S),5β]-3-[[4-[bis[2-[bis[2-(1,1-dimethylethoxy)-2-oxoethyl]amino]ethyl]amino]-5-(1,1-dimethylethoxy)-1,5-dioxopentyl][2-(1,1-dimethylethoxy)-2-oxoethyl]amino]cholan-24-oic acid methyl ester Diisopropylethylamine (19.5 g; 26.2 mL; 151 mmol) is added dropwise in 20 min to a solution of compound A) (33.0 g; 65.5 mmol), N,N-bis[2-[bis[2-(1,1-dimethylethoxy)-2-oxoethyl]amino]ethyl]-L-glutamic acid 1-(1,1-dimethylethyl) ester (prepared as described in WO-A-95/32741: example 15) (53.8 g; 72.1 mmol) and (1-hydroxy-1H-benzotriazolate-O)tris(N-methylmethanaminate)phosphorous(1+) hexafluorophosphate (1−) (BOP) (40.6 g; 91.8 mmol) in DMF (400 mL), stirred at room temperature under nitrogen. After 2 days the reaction mixture is concentrated and taken up in AcOEt. The solution is washed with $H_2O$, dried ($Na_2SO_4$) and evaporated. The crude is purified twice by flash chromatography to give 38.7 g of the desired product (31.4 mmol).

Yield: 48%.
$[α]^{22}D$=−54.50 (c 2.51, $CHCl_3$)
TLC: Stationary phase: silica gel plate 60F 254 Merck
Eluent: 7:3=n-hexane/AcOEt $R_f$=0.22
The $^1$H-NMR, $^{13}$C-NMR, IR and MS spectra are consistent with the indicated structure.

C) [3β(S),5β]-3-[[4-[bis[2-[bis(Carboxymethyl)amino]ethyl]amino]-4-carboxy-1-oxobutyl](carboxymethyl)amino]cholan-24-oic acid A solution of compound B) (38.7 g; 31.4 mmol) in EtOH (350 mL), stirred at room temperature, is added dropwise in 1 h with 500 mL of a 2 N LiOH solution. After 16 h the reaction mixture is concentrated to 500 mL and a 2 N LiOH solution is added again, heating to 50° C. After 24 h the reaction mixture is cooled to room temperature and dropped into 320 mL of 6 N HCl stirred vigorously at 50° C. The pH of the resulting suspension is adjusted to 1.0 with 55 mL of 2 N NaOH. The solid is filtered, washed with 0.1 N HCl and dried. The crude is suspended in $H_2O$ and solubilised by addition of 1 N NaOH, then the basic solution is dropped into a 0.5 N HCl solution. The precipitate is filtered, washed with 0.05 N HCl, $H_2O$ and dried to give 23.5 g of the desired product (26.7 mmol).

Yield: 85% p. f.: 178–182° C.
K.F.: <0.1%
$[α]^{405}{}_{20}$=+24.10 (c 1.49, 1 N NaOH)
HPLC assay: 100% (% area)
Stationary phase: Hypurity Elite C-18 5 μm; column 250×4.6 mm;
Temperature: 40° C.;
Mobile phase: gradient elution;
A=0.01 M $KH_2PO_4$, 0.3 mM EDTA in water
B=$CH_3CN$

| Gradient: | min | % A | % B |
|---|---|---|---|
| | 0 | 95 | 5 |
| | 40 | 65 | 35 |
| | 50 | 65 | 35 |

Flow rate: 1 mL min$^{-1}$;
Detection (UV): 210 nm.

| Elementary analysis | C | H | N | Na | Cl |
|---|---|---|---|---|---|
| % calc.: | 58.62 | 7.78 | 6.36 | | |
| % found: | 57.71 | 8.07 | 6.20 | 0.13 | 0.55 |

The $^1$H-NMR, $^{13}$C-NMR, IR and MS spectra are consistent with the indicated structure.

D) Gadolinium Complex of [3β(S),5β]-3-[[4-[bis[2-[bis(carboxymethyl)amino]ethyl]amino]-4-carboxy-1-oxobutyl](carboxymethyl)amino]cholan-24-oic acid Salified with 1-deoxy-1-(methylamino)-D-glucitol (1:4)

A suspension of the compound prepared at step C) (12.9 g; 14.6 mmol) in $H_2O$ (100 mL) is added with a 1 M meglumine aqueous solution (72.0 mL; 72.0 mmol) at room temperature to give a clear solution having pH 6.2. A 0.393 M $GdCl_3$ aqueous solution (37.2 mL; 14.6 mmol) is added dropwise, keeping pH 6.2 by addition of 1 M meglumine (30.0 mL; 30.0 mmol) by means of a pH-stat. At the end of the additions the reaction mixture is filtered through paper and then through Millipore® filter (HAWP 0.45 μm), nanofiltered, adjusted to pH 7.0 by addition of 1 M meglumine (0.20 mL; 0.20 mmol) and evaporated. The solid is dried ($P_2O_5$; 40° C.) to give 24.0 g of the desired product (13.2 mmol).

Yield: 91% m.p.: 90–92° C.
K.F.: 6.61%
HPLC assay: 100% (% area)
Stationary phase: Lichrospher 100 RP-8 5 μm; column Merck KGAa 250×4 mm;
Temperature: 40° C.;
Mobile phase: isocratic elution with premixed mobile phase: 1 g of n-octylamine is added to 400 mL of acetonitrile and 600 mL of water. The solution is buffered to pH 6 with $H_3PO_4$;
Flow rate: 1 mL min$^{-1}$;
Detection (UV): 210 nm.

| Elementary analysis | C | H | N | Gd | Na | Cl |
|---|---|---|---|---|---|---|
| % calc.: | 46.96 | 7.38 | 6.17 | 8.66 | | |
| % found: | 44.27 | 7.59 | 5.76 | 8.21 | <0.1 | <0.1 |

The IR and MS spectra are consistent with the indicated structure.

EXAMPLE 8

Measurements of the Relaxation Rate ($\Delta 1/T_1$)

The effectiveness of the compounds of the invention as blood pool agents was evaluated by plotting the progress of the longitudinal relaxation rate $1/T_1$ versus the time elasped after the administration. The proton relaxation rate $1/T_1$ of blood samples, collected at predetermined times, was measured at 39° C. by means of a Brucker Minispec PC120 instrumentation using "inversion recovery" three parameter sequences.

The compound prepared in Example 1, gadolinium comples of [3β(S),5β]-3-[[4-[bis[2-[bis(carboxymethyl)amino]ethyl]amino]-4-carboxy-1-oxobutyl]amino]cholan-24-oic acid salified with 1-deoxy-1-(methylamino)-D-glucitol (1:3), was administered to a rabbit at a dose of 0.1 mmol/kg. The following diagram represents the profile of the relaxation rate.

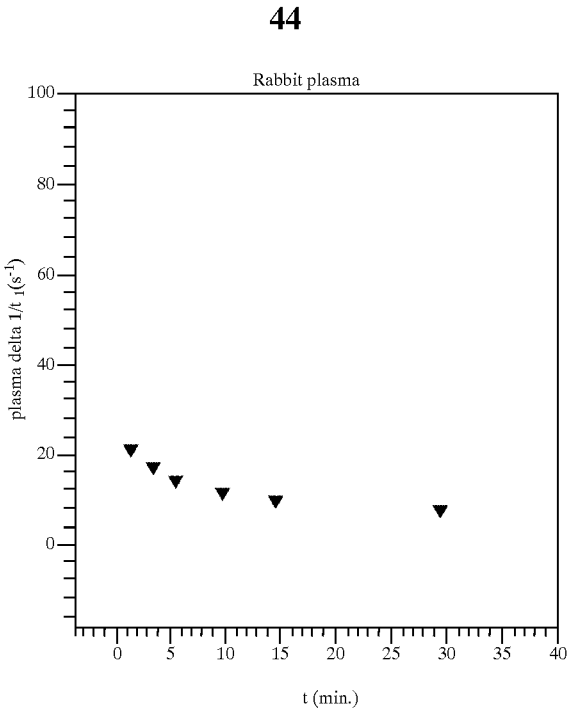

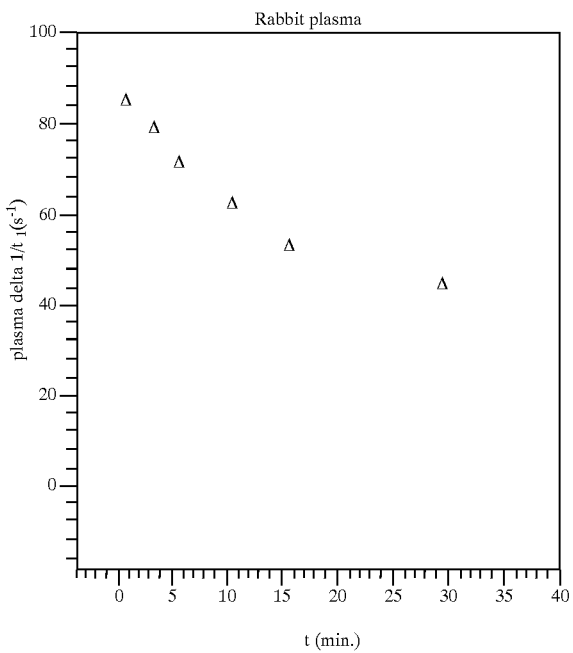

The compound prepared in Example 9 of patent application WO 95/32741, gadolinium complex of (3β,5β,7α,12α)-3-[[N-[N-[2-[[2-[bis(carboxymethyl)amino]ethyl](carboxymethyl)amino]ethyl]-N-(carboxymethyl)-glycyl]glycyl]amino]-7,12-dihydroxy-cholan-24-oic acid salified with 1-deoxy-1-(methylamino)-D-glucitol (1:2), was administered to a rabbit at a dose of 0.1 mmol/kg.

The compound prepared in Example 15 of patent application WO 95/32741, gadolinium complex of [3β(S),5β,7α,12α]-3-[[4-[bis[2-[bis(carboxymethyl)amino]ethyl]amino]-4-carboxy-1-oxobutyl]amino]-7,12-dihydroxycholan-24-oic acid salified with 1-deoxy-1-(methylamino)-D-glucitol (1:3), was administered to the rabbit at a dose of 0.1 mmol/kg.

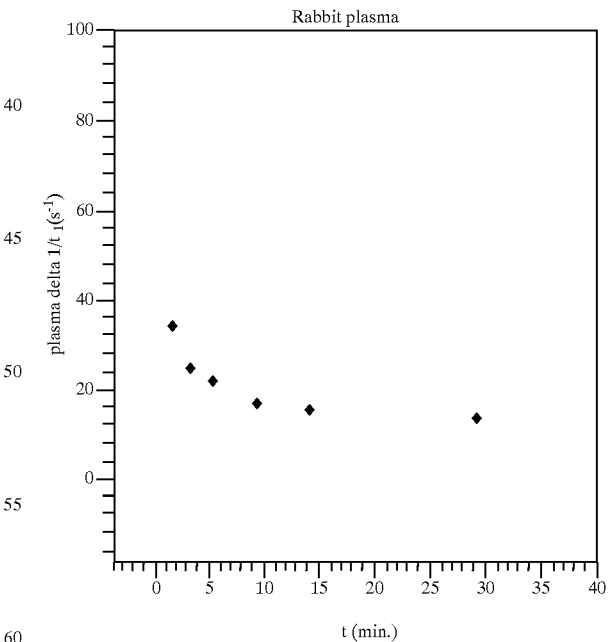

The compound prepared in Example 4, gadolinium complex of [[3β(S),5β,12α]-3-[[4-[bis[2-[bis(carboxymethyl)amino]ethyl]amino]-4-carboxy-1-oxobutyl] amino]-12-hydroxycholan-24-oic acid salified with 1-deoxy-1-(methylamino)-D-glucitol (1:3), was administered to the monkey at a dose of 0.05 mmol/kg. The following diagram is the profile of the relaxation rate.

Monkey plasma

[Graph: plasma delta $1/t_1$ ($s^{-1}$) vs t (min.)]

EXAMPLE 9

0.3 M Pharmaceutical Formulation of the Gadolinium Complex with [3β(S),5β,12α]-3-[[4-[bis[2-[bis(carboxymethyl)amino]ethyl]amino]-4-carboxy-1-oxobutyl]amino]-12-hydroxycholan-24-oic acid Salified with 1-deoxy-1-(methylamino)-D-glucitol (1:3)

31.775 kg of the gadolinium complex of [3β(S),5β,12α]-3-[[4-[bis[2-[bis(carboxymethyl)amino]ethyl]amino]-4-carboxy-1-oxobutyl]amino]-12-hydroxycholan-24-oic acid salified with 1-deoxy-1-(methylamino)-D-glucitol (1:3) (prepared as exemplified in Example 4) and 100 g of trometamol hydrochloride are dissolved in 100 L of sterile water at room temperature in a pharmaceutical stainless steel reactor. After dissolution, the pH of the solution is adjusted to 7.4 by addition of 1 M trometamol. The solution is sterile filtered through filters of 0.22 mm diameter and distributed in 20 mL vials, which are closed with halobutyl plugs, sealed with aluminium ring and vapour sterilized at Fo=18. HPLC shows a 0.294 M titre.

EXAMPLE 10

Pre-filled Syringes Plastic Containing the Formulation of Example 9

20 mL Portions of the solution prepared in Example 9 are placed in a CZ plastic syringe with the tip closed by a cap. The piston is inserted under vacuum and the pre-filled syringe is sterilized in autoclave, with counterbalanced counterpressure, to a value of Fo=18.

What is claimed is:

1. A method for NMR imaging the blood pool system of a human or animal body which comprises: (1) administering to the human or animal to be imaged a chelated complex of bi-travalent paramagnetic metal ion selected from the group consisting of $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $Yb^{(3+)}$ or $Mn^{(2+)}$ with a compound of formula (I), or the salts thereof with a physiologically compatible organic base selected from a primary, secondary, tertiary amine or basic amino acid, or with an inorganic base whose cations are sodium, potassium, magnesium, calcium, or mixtures thereof:

$$X-L-Y \qquad (I),$$

wherein:

X is DTPA substituted on the central chain (IVa)

[Chemical structure of DTPA derivative with HOOC groups and L-Y linkage]

Y is selected from the group consisting of cholic, deoxycholic, chenodeoxycholic and lithocholic residues, and L has the structure (III)

$$\left[\left\{CH_2\right\}_p\left\{O\right\}_q\left\{Z\right\}_n\right]_m$$

wherein:

m is 1 to 10, n and q are independently 0 or 1, provided they are not both zero, p is 0 to 10, Z is an oxygen atom or a —NR group, in which R is a hydrogen atom, or a ($C_1$–$C_5$) alkyl group unsubstituted or substituted by a group —COOH, provided that L is not linked to the 24 position of Y, and thereafter (2) NMR imaging the human or animal body.

2. The method of claim 1 wherein R is a group —COOH and L has the structures (IIIa) or (IIIb)

(IIIa)

[Chemical structure]

(IIIb)

[Chemical structure with COOH]

3. The method of claim 1 wherein the compound is selected from the group consisting of:

[3β(S),5β]-3-[[4-[bis[2-[bis(carboxymethyl)amino]ethyl]-amino]-4-carboxy-1-oxo-butyl](carboxymethyl)amino]cholan-24-oic acid;

[3β(S),5β]-3-[[4-[bis[2-[bis(carboxymethyl)amino]ethyl]-amino]-4-carboxy-1-oxo-butyl]amino]cholan-24-oic acid;

[3β(S),5β]-3-[[4-[bis[2-[bis(carboxymethyl)amino]-ethyl]amino]-4-carboxy-1-oxobutyl]amino]-12-oxocholan-24-oic acid;

[3β(S),5β,7α]-3-[[4-bis[2-[bis(carboxymethyl)amino]-ethyl]amino]-4-carboxyl-1-oxobutyl]amino]-7-hydroxycholan-24-oic acid;

2-[[[3β(S),5β]-3-[[4-[bis[2-[bis(carboxymethyl)amino]-ethyl]amino]-4-carboxyl-1-oxobutyl]amino]-24-oxocholan-24-yl]amino]ethanesulfonic acid;

[3β(S),5β,12α]-3-[[4-[bis[2-[bis(carboxymethyl)amino]-ethyl]amino]-4-carboxyl-1-oxobutyl]amino]-12-hydroxycholan-24-oic acid;

[3α(S),5β]-3-[2-[[5-[bis[2-[bis(carboxymethyl)amino]-ethyl]amino]-5-carboxypentyl]amino]-2-oxoethoxy]cholan-24-oic acid;

[3β(S),5β,7α,12α]-3-[[4-[bis[2-[bis(carboxymethyl)amino]-ethyl]amino]-4-carboxy-1-oxobutyl]amino]-7,12-dihydroxy-cholan-24-oic acid; and

[3β(S),5β,7α,12α]-3-[[4-[[5-[bis[2-[bis(carboxymethyl)-amino]ethyl]amino]-5-carboxypentyl]amino]-1,4-dioxobutyl]amino]-7,12-dihydroxycholan-24-oic acid.

4. The method of claim 1 wherein the complexes are formed with gadolinium or magnesium ions.

5. The method of claim 1 wherein the chelated complex salts are formed with sodium and N-methylglucamine.

6. A method for NMR imaging the blood pool system of a human or animal body which comprises (1) administering to the human or animal to be imaged a chelated complex of bi-travalent paramagnetic metal ion selected from the group consisting of $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $Yb^{(3+)}$ or $Mn^{(2+)}$ with [3β(S),5β,12α]-3-[[4-[bis[2-[bis(carboxymethyl)amino]-ethyl]amino]-4-carboxy-1-oxobutyl]amino]-12-hydroxycholan-24-oic acid or the salts thereof with a physiologically compatible organic base selected from a primary, secondary, tertiary amine or basic amino acid, or with an inorganic base whose cations are sodium, potassium, magnesium, calcium, or mixtures thereof and thereafter (2) NMR imaging the human or animal body.

* * * * *

UNITED STATES PATENT AND TRADEMARK OFFICE
CERTIFICATE OF CORRECTION

PATENT NO.   : 6,461,588 B1
DATED        : October 8, 2002
INVENTOR(S)  : Anelli et al.

It is certified that error appears in the above-identified patent and that said Letters Patent is hereby corrected as shown below:

<u>Column 48,</u>
Line 2, change "magnesium" to -- manganese --.

Signed and Sealed this

Eighteenth Day of February, 2003

JAMES E. ROGAN
*Director of the United States Patent and Trademark Office*